US010604563B2

(12) United States Patent
Liang et al.

(10) Patent No.: US 10,604,563 B2
(45) Date of Patent: Mar. 31, 2020

(54) NUCLEIC ACIDS ENCODING ANTI-COMPLEMENT FACTOR BB ANTIBODIES

(71) Applicant: Allergan, Inc., Irvine, CA (US)

(72) Inventors: Yanbin Liang, Irvine, CA (US); Chen Li, Irvine, CA (US); Iris Lee, La Canada, CA (US); Victor M. Guzman, Santa Ana, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 16/142,421

(22) Filed: Sep. 26, 2018

(65) Prior Publication Data

US 2019/0071492 A1    Mar. 7, 2019

Related U.S. Application Data

(62) Division of application No. 15/790,759, filed on Oct. 23, 2017, now Pat. No. 10,093,724, which is a division of application No. 14/631,057, filed on Feb. 25, 2015, now Pat. No. 9,796,776.

(60) Provisional application No. 61/945,613, filed on Feb. 27, 2014, provisional application No. 61/947,880, filed on Mar. 4, 2014.

(51) Int. Cl.
| | |
|---|---|
| *C12N 15/13* | (2006.01) |
| *C12N 15/12* | (2006.01) |
| *C07K 16/18* | (2006.01) |
| *A61K 39/00* | (2006.01) |

(52) U.S. Cl.
CPC ........ *C07K 16/18* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 5,679,546 A | 10/1997 | Ko et al. | |
| 7,341,839 B2 | 3/2008 | Hollyfield et al. | |
| 7,351,524 B2 | 4/2008 | Hageman | |
| 7,959,919 B2 | 6/2011 | Bansal ................ | A61K 38/04 424/130.1 |
| 9,243,070 B2 | 1/2016 | Bansal ................ | C07K 16/18 |
| 9,796,776 B2 | 10/2017 | Liang ................. | C07K 16/18 |
| 2004/0110226 A1 | 6/2004 | Lazar ................. | C07K 16/00 435/7.1 |
| 2005/0107319 A1 | 5/2005 | Bansal | |
| 2008/0075720 A1 | 3/2008 | Holers et al. | |
| 2008/0299114 A1 | 12/2008 | Emlen et al. | |
| 2009/0081211 A1 | 3/2009 | Campagne | |
| 2009/0214538 A1* | 8/2009 | Fung ................... | A61K 39/395 424/135.1 |
| 2010/0239573 A1* | 9/2010 | Bansal ................ | C07K 16/18 424/133.1 |
| 2010/0291106 A1 | 11/2010 | Etemad-Gilbertson et al. | |

FOREIGN PATENT DOCUMENTS

| | | |
|---|---|---|
| WO | 2007-056227 | 5/2007 |
| WO | 2009-029669 | 3/2009 |
| WO | 2010029162 A1 | 3/2010 |
| WO | 2012075023 A2 | 6/2012 |
| WO | 2013-0152020 | 10/2013 |
| WO | 2013-0177035 | 11/2013 |

OTHER PUBLICATIONS

D'Angelo et al., Many Routes to an Antibody Heavy-Chain CDR3: Necessary, Yet Insufficient, for Specific Binding, Frontiers in Immunology vol. 9, Article 395 Mar. 2018; doi:10.3389/fimmu.2018.00395. (Year: 2018).*
Piche-Nicholas et al., Changes in complemetarity-determining regions significantly alter IgG binding to the neonatal Fc receptor (FcRN) and pharmacokinetics, MABS 2018, vol. 10, No. 1, 81-94, doi.org/10.1080/19420862.2017.1389355. (Year: 2018).*
Rudlkoff et al., Proc Natl Acad Sci USA 79: 1979-1983 (1982).
Colman, Research in Immunology 145: 33-36 (1994).
Kussie et al., J. Immunol. 152: 146-152 (1994).
Chen et al., EMBO J., 14: 2784-2794 (1995).
Fishelson, Ziv et al., Residual Hemolytic and Proteloytic Activity Expressed by Bb After Decay-Dissociation of C3b,Bb1, The Journal of Immunology, Mar. 1984, pp. 1425-1429, vol. 132, No. 3, The American Association of Immunologists.
Leinhase, Iris et al., Inhibition of the Alternative Complement Activation Pathway in Traumatic Brain Injury by a Monoclonal Anti-Factor B Antibody: A Randomized Placebo-Controlled Study in Mice, Journal of Neuroinflammation, May 2, 2007, pp. 1-12, vol. 4, No. 13.
Scholl, Hendrick P.N. et al., Systemic Complement Activation in Age-Related Macular Degeneration, PLOS ONE, Jul. 8, 2008, e2593, pp. 1-7, vol. 3, Issue 7, www.plosone.org.
Sivaprasad, Sobha et al., Estimation of Systemic Complement C3 Activity in Age-Related Macular Degeneration, Arch Opthalmol, Apr. 2007, pp. 515-519, vol. 125, American Medical Association.

* cited by examiner

*Primary Examiner* — Phillip Gambel
(74) *Attorney, Agent, or Firm* — Rosemarie Pilpa

(57) ABSTRACT

The present disclosure relates to antibodies and polynucleotides encoding the same, which may be used to prevent, control, or reduce the activity of the complement pathway. In addition, the disclosure is directed to compositions and methods for diagnosing and treating diseases mediated by or involving complement Factor Bb. Specifically, the disclosure is related to anti-complement Factor Bb antibodies.

9 Claims, 3 Drawing Sheets

Specification includes a Sequence Listing.

A Diagram of the Structure of Complement Factor B

SEQUENCE LISTING

<160> NUMBER OF SEQ ID NOS: 38

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Asp Ile Phe Ser Ser His Trp
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Ile Leu Pro Arg Ser Gly Ile Thr His Tyr Asn Glu Asn Phe Asn
1               5                   10                  15

Gly

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ile Asn Trp Glu Asp Ser
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Ala Ser Gln Asn Val Asn Val Trp Leu
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Lys Ala Ser Asn Leu His Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Gly Gln Ser Tyr Pro Tyr Thr
1               5

<210> SEQ ID NO 7
<211> LENGTH: 505
<212> TYPE: PRT
<213> ORGANISM: Homo sapiens

<400> SEQUENCE: 7

Lys Ile Val Leu Asp Pro Ser Gly Ser Met Asn Ile Tyr Leu Val Leu
1               5                   10                  15

Asp Gly Ser Asp Ser Ile Gly Ala Ser Asn Phe Thr Gly Ala Lys Lys
            20                  25                  30

Cys Leu Val Asn Leu Ile Glu Lys Val Ala Ser Tyr Gly Val Lys Pro
        35                  40                  45

Arg Tyr Gly Leu Val Thr Tyr Ala Thr Tyr Pro Lys Ile Trp Val Lys
    50                  55                  60

Val Ser Glu Ala Asp Ser Ser Asn Ala Asp Trp Val Thr Lys Gln Leu
65                  70                  75                  80

Asn Glu Ile Asn Tyr Glu Asp His Lys Leu Lys Ser Gly Thr Asn Thr
                85                  90                  95

Lys Lys Ala Leu Gln Ala Val Tyr Ser Met Met Ser Trp Pro Asp Asp
            100                 105                 110

Val Pro Pro Glu Gly Trp Asn Arg Thr Arg His Val Ile Ile Leu Met
        115                 120                 125

Thr Asp Gly Leu His Asn Met Gly Gly Asp Pro Ile Thr Val Ile Asp
    130                 135                 140

Glu Ile Arg Asp Leu Leu Tyr Ile Gly Lys Asp Arg Lys Asn Pro Arg
145                 150                 155                 160

Glu Asp Tyr Leu Asp Val Tyr Val Phe Gly Val Gly Pro Leu Val Asn
                165                 170                 175

Gln Val Asn Ile Asn Ala Leu Ala Ser Lys Lys Asp Asn Glu Gln His
            180                 185                 190

Val Phe Lys Val Lys Asp Met Glu Asn Leu Glu Asp Val Phe Tyr Gln
        195                 200                 205

Met Ile Asp Glu Ser Gln Ser Leu Ser Leu Cys Gly Met Val Trp Glu
    210                 215                 220

His Arg Lys Gly Thr Asp Tyr His Lys Gln Pro Trp Gln Ala Lys Ile
225                 230                 235                 240

Ser Val Ile Arg Pro Ser Lys Gly His Glu Ser Cys Met Gly Ala Val
                245                 250                 255

Val Ser Glu Tyr Phe Val Leu Thr Ala Ala His Cys Phe Thr Val Asp
            260                 265                 270

Asp Lys Glu His Ser Ile Lys Val Ser Val Gly Gly Glu Lys Arg Asp
        275                 280                 285

Leu Glu Ile Glu Val Val Leu Phe His Pro Asn Tyr Asn Ile Asn Gly
    290                 295                 300

Lys Lys Glu Ala Gly Ile Pro Glu Phe Tyr Asp Tyr Asp Val Ala Leu
305                 310                 315                 320

Ile Lys Leu Lys Asn Lys Leu Lys Tyr Gly Gln Thr Ile Arg Pro Ile
                325                 330                 335

Cys Leu Pro Cys Thr Glu Gly Thr Thr Arg Ala Leu Arg Leu Pro Pro
                340                 345                 350

Thr Thr Thr Cys Gln Gln Gln Lys Glu Glu Leu Leu Pro Ala Gln Asp
            355                 360                 365

Ile Lys Ala Leu Phe Val Ser Glu Glu Lys Lys Leu Thr Arg Lys
370                 375                 380

Glu Val Tyr Ile Lys Asn Gly Asp Lys Lys Gly Ser Cys Glu Arg Asp
385                 390                 395                 400

Ala Gln Tyr Ala Pro Gly Tyr Asp Lys Val Lys Asp Ile Ser Glu Val
                405                 410                 415

Val Thr Pro Arg Phe Leu Cys Thr Gly Gly Val Ser Pro Tyr Ala Asp
            420                 425                 430

Pro Asn Thr Cys Arg Gly Asp Ser Gly Gly Pro Leu Ile Val His Lys
        435                 440                 445

Arg Ser Arg Phe Ile Gln Val Gly Val Ile Ser Trp Gly Val Val Asp
    450                 455                 460

Val Cys Lys Asn Gln Lys Arg Gln Lys Gln Val Pro Ala His Ala Arg
465                 470                 475                 480

Asp Phe His Ile Asn Leu Phe Gln Val Leu Pro Trp Leu Lys Glu Lys
                485                 490                 495

Leu Gln Asp Glu Asp Leu Gly Phe Leu
                500                 505

<210> SEQ ID NO 8
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Val Asn Val Trp
            20                  25                  30

Leu Ser Trp Tyr Gln Gln Lys Pro Gly Lys Ala Pro Lys Leu Leu Ile
        35                  40                  45

Phe Lys Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr

```
                    180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 9
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Thr Val Thr Ile Thr Cys Arg Ala Ser Gln Asn Val Asn Val Trp
            20                  25                  30

Leu Ser Trp Tyr Gln Gln Lys Pro Gly Lys Ala Pro Lys Leu Leu Ile
        35                  40                  45

Phe Lys Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Ser Leu Ser Ala Ser Val Gly
1               5                   10                  15

Asp Thr Val Thr Ile Thr Cys Arg Ala Ser Gln Asn Val Asn Val Trp
            20                  25                  30

Leu Ser Trp Tyr Gln Gln Lys Pro Gly Lys Ala Pro Lys Leu Leu Ile
```

```
                35                  40                  45
Phe Lys Ala Gly Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gln Ser Tyr Pro Tyr
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Ser Leu Ser Ala Ser Val Gly
 1               5                  10                  15

Asp Thr Val Thr Ile Thr Cys Arg Ala Ser Gln Ser Val Asn Val Trp
                20                  25                  30

Leu Ser Trp Tyr Gln Gln Lys Pro Gly Lys Ala Pro Lys Leu Leu Ile
            35                  40                  45

Phe Lys Ala Gly Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Gln Ser Tyr Pro Tyr
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Asp Ile Phe Ser Ser His
            20                  25                  30

Trp Ile Glu Trp Ile Arg Gln Ala Pro Gly Gln Gly Leu Glu Trp Met
        35                  40                  45

Gly Glu Ile Leu Pro Arg Ser Gly Ile Thr Asn Tyr Ala Gln Lys Phe
    50                  55                  60

Gln Gly Arg Val Thr Phe Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Asn Trp Glu Asp Ser Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Leu
    210                 215                 220

<210> SEQ ID NO 13
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Asp Ile Phe Ser Ser His
            20                  25                  30

Trp Ile Glu Trp Ile Arg Gln Ala Pro Gly Gln Gly Leu Glu Trp Met
            35                  40                  45

Gly Glu Ile Leu Pro Arg Ser Gly Ile Thr His Tyr Ala Glu Lys Phe
 50                  55                  60

Gln Gly Arg Val Thr Phe Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Asn Trp Glu Asp Ser Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Leu
    210                 215                 220

<210> SEQ ID NO 14
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Asp Gly Asp Ile Phe Ser Ser His
            20                  25                  30

Trp Ile Glu Trp Ile Arg Gln Ala Pro Gly Gln Gly Leu Glu Trp Met
            35                  40                  45

Gly Glu Ile Leu Pro Arg Ser Gly Ile Thr His Tyr Ala Glu Lys Phe
 50                  55                  60

Gln Gly Arg Val Thr Phe Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Asn Trp Glu Asp Ser Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

-continued

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
            195                 200                 205

Asp Lys Lys Val Glu Pro Lys Ser Cys Asp Lys Thr His Leu
            210                 215                 220

<210> SEQ ID NO 15
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Asp Gly Asp Ile Phe Ser Ser His
            20                  25                  30

Trp Ile Glu Trp Val Arg Gln Ala Pro Gly Gln Gly Leu Glu Trp Met
        35                  40                  45

Gly Glu Ile Leu Pro Arg Ser Gly Ile Thr Asn Tyr Ala Glu Lys Phe
    50                  55                  60

Gln Gly Arg Val Thr Phe Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Asn Trp Glu Asp Ser Trp Gly Gln Gly Thr Leu Val Thr Val
            100                 105                 110

Ser Ser Ala Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Leu
    210                 215                 220

<210> SEQ ID NO 16
<211> LENGTH: 764
<212> TYPE: PRT
<213> ORGANISM: Homo sapiens

<400> SEQUENCE: 16

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

```
Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
                100                 105                 110

Glu Tyr Trp Pro Arg Ser Pro Tyr Tyr Asn Val Ser Asp Glu Ile Ser
            115                 120                 125

Phe His Cys Tyr Asp Gly Tyr Thr Leu Arg Gly Ser Ala Asn Arg Thr
        130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
                180                 185                 190

Arg Gly Leu Thr Leu Arg Gly Ser Gln Arg Arg Thr Cys Gln Glu Gly
                195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr
            260                 265                 270

Leu Val Leu Asp Gly Ser Asp Ser Ile Gly Ala Ser Asn Phe Thr Gly
            275                 280                 285

Ala Lys Lys Cys Leu Val Asn Leu Ile Glu Lys Val Ala Ser Tyr Gly
    290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
                340                 345                 350

Thr Asn Thr Lys Lys Ala Leu Gln Ala Val Tyr Ser Met Met Ser Trp
            355                 360                 365

Pro Asp Asp Val Pro Pro Glu Gly Trp Asn Arg Thr Arg His Val Ile
    370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
                435                 440                 445

Glu Gln His Val Phe Lys Val Lys Asp Met Glu Asn Leu Glu Asp Val
450                 455                 460
```

```
Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
            485                 490                 495

Ala Lys Ile Ser Val Ile Arg Pro Ser Lys Gly His Glu Ser Cys Met
                500                 505                 510

Gly Ala Val Ser Glu Tyr Phe Leu Thr Ala Ala His Cys Phe
            515                 520                 525

Thr Val Asp Asp Lys Glu His Ser Ile Lys Val Ser Val Gly Gly Glu
        530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
        595                 600                 605

Leu Pro Pro Thr Thr Thr Cys Gln Gln Gln Lys Glu Glu Leu Leu Pro
610                 615                 620

Ala Gln Asp Ile Lys Ala Leu Phe Val Ser Glu Glu Glu Lys Lys Leu
625                 630                 635                 640

Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
        675                 680                 685

Tyr Ala Asp Pro Asn Thr Cys Arg Gly Asp Ser Gly Gly Pro Leu Ile
        690                 695                 700

Val His Lys Arg Ser Arg Phe Ile Gln Val Gly Val Ile Ser Trp Gly
705                 710                 715                 720

Val Val Asp Val Cys Lys Asn Gln Lys Arg Gln Lys Gln Val Pro Ala
                725                 730                 735

His Ala Arg Asp Phe His Ile Asn Leu Phe Gln Val Leu Pro Trp Leu
            740                 745                 750

Lys Glu Lys Leu Gln Asp Glu Asp Leu Gly Phe Leu
                755                 760

<210> SEQ ID NO 17
<211> LENGTH: 259
<212> TYPE: PRT
<213> ORGANISM: Homo sapiens

<400> SEQUENCE: 17

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
            20                  25                  30

Pro Gln Gly Ser Cys Ser Leu Glu Gly Val Glu Ile Lys Gly Gly Ser
        35                  40                  45

Phe Arg Leu Leu Gln Glu Gly Gln Ala Leu Glu Tyr Val Cys Pro Ser
    50                  55                  60

Gly Phe Tyr Pro Tyr Pro Val Gln Thr Arg Thr Cys Arg Ser Thr Gly
65                  70                  75                  80
```

Ser Trp Ser Thr Leu Lys Thr Gln Asp Gln Lys Thr Val Arg Lys Ala
            85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
    130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Tyr Tyr Met Ser
1               5

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Ser Arg His Arg Val Tyr Gly Tyr Thr Pro Glu Tyr Ser Ala Ser
1               5                   10                  15

Val Lys Gly

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Asn Pro Gly Tyr Tyr Ala Met Asp Tyr
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Ala Ser Gln Ser Val Asp Tyr Asp Gly Asp Ser Tyr Met Asn
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Ser Asn Leu Glu Ser
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Gln Ser Asn Ala Asp Pro Tyr Thr
1               5

<210> SEQ ID NO 24
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
            20                  25                  30

Gly Asp Ser Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Asn
                85                  90                  95

Ala Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr

```
              130                 135                 140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
            210                 215

<210> SEQ ID NO 25
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Asp Tyr Asp
                20                  25                  30

Gly Asp Ser Tyr Met Asn Trp Tyr Gln Gln Lys Pro Gly Gln Ala Pro
            35                  40                  45

Arg Leu Leu Ile Tyr Ala Ala Ser Asn Leu Glu Ser Gly Ile Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Gly Ala Thr Tyr Tyr Cys Gln Gln Ser Asn
                85                  90                  95

Ala Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
                195                 200                 205

Val Thr Lys Ser Phe Asn Arg Gly Glu Cys
            210                 215

<210> SEQ ID NO 26
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 26

```
Glu Ile Val Leu Thr Gln Ser Pro Ala Thr Leu Ser Leu Ser Pro Gly
1               5                   10                  15

Glu Arg Ala Thr Leu Gly Cys Lys Ala Ser Gln Ser Val Asp Tyr Asp
            20                  25                  30

Gly Asp Ser Tyr Met Asn Trp Tyr Gln Gln Lys Pro Gly Gln Ala Pro
        35                  40                  45

Arg Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Asn
                85                  90                  95

Ala Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 27
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

```
Glu Ile Val Leu Thr Gln Ser Pro Ala Thr Leu Ser Leu Ser Pro Gly
1               5                   10                  15

Glu Arg Ala Thr Leu Gly Cys Lys Ala Ser Gln Ser Val Asp Tyr Asp
            20                  25                  30

Gly Asp Ser Tyr Met Asn Trp Tyr Gln Gln Lys Pro Gly Gln Ala Pro
        35                  40                  45

Arg Leu Leu Ile Tyr Ala Ala Ser Asn Arg Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln Gln Ser Asn
                85                  90                  95

Ala Asp Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215
```

<210> SEQ ID NO 28
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Arg Asp Tyr
            20                  25                  30

Tyr Met Ser Trp Val Arg Gln Ala Pro Gly Lys Gly Leu Glu Trp Val
        35                  40                  45

Gly Phe Ser Arg His Arg Val Tyr Gly Tyr Thr Thr Glu Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Pro Gly Tyr Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Leu
225
```

<210> SEQ ID NO 29
<211> LENGTH: 229
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Arg Asp Tyr
            20                  25                  30

Tyr Met Ser Trp Val Arg Gln Ala Pro Gly Lys Gly Leu Glu Trp Leu
        35                  40                  45

Gly Phe Ser Arg His Arg Val Tyr Gly Tyr Thr Pro Glu Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Pro Gly Tyr Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Leu
225

<210> SEQ ID NO 30
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Gly Thr Thr Gly Phe Thr Phe Arg Asp Tyr
            20                  25                  30

Tyr Met Ser Trp Val Arg Gln Ala Pro Gly Lys Gly Leu Glu Trp Leu
        35                  40                  45

Gly Phe Ser Arg His Arg Val Tyr Gly Tyr Thr Pro Glu Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Lys Thr Glu Asp Thr Ala Val Tyr
                85                  90                  95
```

Tyr Cys Ala Arg Asp Asn Pro Gly Tyr Tyr Ala Met Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Leu
225

<210> SEQ ID NO 31
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Gly Thr Thr Gly Phe Thr Phe Arg Asp Tyr
            20                  25                  30

Tyr Met Ser Trp Val Arg Gln Ala Pro Gly Lys Gly Leu Glu Trp Leu
        35                  40                  45

Gly Phe Ser Arg His Arg Ala Tyr Gly Tyr Thr Pro Glu Tyr Ala Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Pro Gly Tyr Tyr Ala Met Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys

```
            210                 215                 220
Asp Lys Thr His Leu
225

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 32

Gly Asp Ile Phe Ser Ser His Trp
1               5

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 33

Glu Ile Leu Pro Arg Ser Gly Ile Thr His Tyr Asn Glu Asn Phe Asn
1               5                   10                  15

Gly

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 34

Ala Ile Asn Trp Glu Asp Ser
1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 35

His Ala Ser Gln Asn Val Asn Val Trp Leu
1               5                   10

<210> SEQ ID NO 36
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 36

Lys Ala Ser Asn Leu His Thr
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 37

Gln Gln Gly Gln Ser Tyr Pro Tyr Thr
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 38

His His His His His His
1               5
```

NUCLEIC ACIDS ENCODING ANTI-COMPLEMENT FACTOR BB ANTIBODIES

CROSS-REFERENCE

This application is a Divisional of U.S. application Ser. No. 15/790,759, filed Oct. 23, 2017, now U.S. Pat. No. 10,093,724, which is a divisional of U.S. application Ser. No. 14/631,057, filed Feb. 25, 2015, now U.S. Pat. No. 9,796,776, which claims priority under 35 U.S.C. § 119(e) from U.S. Provisional Application Ser. No. 61/945,613, filed Feb. 27, 2014 and U.S. Provisional Application Ser. No. 61/947,880, filed Mar. 4, 2014, each of which is hereby incorporated by reference in its entirety.

TECHNICAL FIELD OF THE INVENTION

The present disclosure relates to anti-complement antibodies and compositions thereof, polynucleotides encoding the same, expression vectors and host cells for production of the antibodies, and compositions and methods for diagnosing and treating diseases mediated by complement. Specifically disclosed are anti-Factor B and anti-Factor Bb antibodies for use in diagnosing and treating Factor B and Factor Bb associated diseases, in particular, Age-Related Macular Degeneration (AMD).

BACKGROUND OF THE INVENTION

The complement system is composed of nearly 50 individual proteins that functions as a part of the innate immune system providing the initial phase of host defense, opsonization of foreign material, and tissue homeostasis. (Ricklin D., 2010, Complement: a Key system for immune surveillance and homeostasis. *Nature: Immunology*, 785-795) The complement system is found in all multicellular organism and phylogenetically predates the formation of the adaptive immune system (Zarkadis I. K., 2001 Phylogenetic aspects of the complement system. *Development and Comparative Immunology*, 745-762.).

Activation of the complement system occurs along three primary pathways: classical, lectin and alternative pathways. During the activation process sequential protein-protein interactions and proteolytic activity leads the generation of the C3 and C5 convertases. These convertases are responsible for producing complement activation split products that represent the effector molecules of the complement cascade important for opsonization, generation of anaphylatoxins, and the formation of the membrane attack complex (MAC). The latter of these is essential for the lytic activity of the complement cascade (Ricklin D., 2010). Under normal conditions activation of the complement cascades provides defense against pathogenic bacterial, as well as clearance of diseased and injured tissue. Normally, the formation of MAC does not affect surrounding tissue due to the presence of cell surface and soluble regulatory components which include CFH, CFH related proteins, C4BP, CD46, CD55, CD59, and complement factor I (CFI). However, when excess activation occurs or when there is a failure to produce complement negative regulatory components, both acute and chronic disease states are induced. Examples in which uncontrolled complement activation is recognized as causative to human pathologies include: Glomerulonephritis, Systemic Lupus Erythematosus, Paroxysomal Nocturnal Hemoglobinuria, Alzheimer's, Hereditary Angioedmea, Myasthenia Gravis and Age-related Macular Degeneration (AMD) (Ricklin & Lambris, 2013, Complement in Immune and inflammatory Disorders: Pathological Mechanisms. *Journal of Immunology*, 3831-3838).

Complement factor B is a protein that circulates in the blood as a single chain polypeptide. Upon activation of the alternative pathway, Factor B (nearly 750 aa) is cleaved by complement Factor D yielding two polypeptides, the smaller, non-catalytic chain Ba (about 230 aa; comprising three complement control protein (CCP) domains) and the larger, catalytic subunit Bb (about 510 aa; comprising a protein interaction domain and a serine protease domain). Factor Bb is a serine protease that associates with C3b to form the alternative pathway's C3 convertase as well as a second protease, C5 convertase, which cleaves the C5 protein into C5a and C5b. Cleavage product C5b initiates the membrane attack pathway, which results in the membrane attack complex (MAC). The MAC is a transmembrane channel, which results in osmotic lysis of the target pathogen. Thus, cleavage of Factor B and production of Factor Bb aids in the complement process.

Factor B is a tightly regulated, highly specific serine protease. In its activated form, it catalyzes the central amplification step of complement activation to initiate inflammatory responses, cell lysis, phagocytosis and B-cell stimulation (Carroll et al., Nat. Immunol. 5:981-986 (2004)). Factor B is activated through an assembly process: it binds surface-bound C3b, or its fluid-phase counterpart C3 ($H_2O$), after which it is cleaved by factor B into fragments Ba (residues 1-234; Factor Ba, Fragment Ba, Complement Factor Ba) and Bb (residues 235-739; Factor Bb, Fragment Bb, Complement Factor Bb). Fragment Ba dissociates from the complex, leaving behind the alternative pathway C3 convertase complex C3b-Bb, which cleaves C3 into C3a and C3b.

Age-related Macular Degeneration (AMD) is the leading cause of blindness in the elderly in the developed nations. In the US population alone the prevalence of advanced forms of AMD are associated with vision loss occurs in nearly 2 million individuals. Another 7 million individuals with intermediate AMD are at a high risk for development of advanced forms of AMD. Inclusion of the European population nearly doubles the number of impacted individuals. AMD is characterized by a progressive loss of vision attributable to a parainflammatory process causing the progressive degeneration of the neuroretina, and support tissues which include the retinal pigmented epithelium (RPE) and choriocapillaris. The majority of clinically significant vision loss occurs when the neurodegenerative changes impact the region of central vision within a highly specialized region of the eye, responsible for fine visual acuity, the macula. The disease has a tremendous impact on the physical and mental health of the individual due to vision loss and increased dependence on family members to perform everyday tasks.

The deregulation of the complement system is highly correlated with the development of AMD. First, genetic mutations in complement genes alter a person's risk of developing AMD. In addition, AMD-related inflammation is associated deregulation of complement activity as indicated by elevation of complement activation products in systemic circulation and in AMD tissues by histopathological analysis. New discoveries, have highlighted the potential pathological impact of the membrane attack complex in disease occurrence (Whitmore S, et al. 2014, Complement activation and choriocapillaris loss in early AMD: Implications for pathphysiology and therapy. Progress in Retinal and Eye Research, Dec. 5, 2014 EPub ahead of print).

The present invention provides anti-Factor Bb antibodies for the prevention and treatment of complement associated diseases, AMD, and other complement-associated eye conditions.

SUMMARY OF THE INVENTION

The invention encompasses methods and compositions comprising an anti-Factor Bb antibody. In one embodiment, the anti-Factor Bb antibody binds to complement Factor Bb with greater affinity than to complement Factor B. In another aspect, the anti-Factor Bb antibody binds to Factor Bb and inhibits complement dependent hemolysis. In another aspect, the anti-Factor Bb antibody binds to complement Factor Bb with a Kd of less than about 1 nM. In another aspect, the anti-Factor Bb antibodies of the invention blocks the formation of membrane attack complex (MAC).

In another embodiment, the anti-Factor Bb antibodies of the invention comprises a first amino acid sequence and a second amino acid sequence with the first amino acid sequence being (i) a CDR1 selected from: (a) a CDR1 amino acid sequence GDIFSSHW, SEQ ID NO:1; (b) a CDR1 amino acid sequence that differs by no more than a total of 2 amino acid additions, deletions, or substitutions selected from GDIFSSHW, SEQ ID NO:1; and (c) a CDR1 amino acid sequence of GDIFSSX$_1$W wherein X$_1$ is Histidine and one other amino acid is substituted with Alanine; (ii) a CDR2 selected from: (a) a CDR2 amino acid sequence EILPRSGITHYNENFNG, SEQ ID NO:2; (b) a CDR2 amino acid sequence that differs by no more than a total of 2 amino acid additions, deletions, or substitutions selected from EILPRSGITHYNENFNG, SEQ ID NO:2; and (c) a CDR2 amino acid sequence of X$_1$IX$_2$PX$_3$SGITHYNENFNG wherein X$_1$ is Glutamic acid, X$_2$ is Leucine, and X$_3$ Arginine, and one other amino acid is substituted with Alanine; and (iii) a CDR3 selected from: (a) a CDR3 amino acid sequence AINWEDS, SEQ ID NO:3; (b) a CDR3 amino acid sequence that differs by no more than a total of 2 amino acid additions, deletions, or substitutions selected from AINWEDS, SEQ ID NO:3; and (c) a CDR3 amino acid sequence of AX$_1$NX$_2$X$_3$X$_4$S wherein X$_1$ is Isoleucine acid, X$_2$ is Tryptophan, X$_3$ Glutamic acid, X$_3$ Aspartic acid, and one other amino acid is substituted with Alanine; and a second amino acid sequence being (i) a CDR1 selected from: (a) a CDR1 amino acid sequence HASQNVNVWL, SEQ ID NO:4; (b) a CDR1 amino acid sequence that differs by no more than a total of 2 amino acid additions, deletions, or substitutions selected from HASQN-VNVWL, SEQ ID NO:4, SEQ ID NO:4; and (c) a CDR1 amino acid sequence of HASQNVNVX$_1$L wherein X$_1$ is Tryptophan and one other amino acid is substituted with Alanine; (ii) a CDR2 selected from: (a) a CDR2 amino acid sequence KASNLHT, SEQ ID NO:5; (b) a CDR2 amino acid sequence that differs by no more than a total of 2 amino acid additions, deletions, or substitutions selected from KASNLHT, SEQ ID NO:5; and (c) a CDR2 amino acid sequence of KASNLHX$_1$ wherein X$_1$ is Threonine one other amino acid is substituted with Alanine; and (iii) a CDR3 selected from: (a) a CDR3 amino acid sequence QQGQSY-PYT, SEQ ID NO:6; (b) a CDR3 amino acid sequence that differs by no more than a total of 2 amino acid additions, deletions, or substitutions selected from QQGQSYPYT, SEQ ID NO:6; and (c) a CDR3 amino acid sequence of QX$_1$GQSYPX$_2$T wherein X$_1$ is Glutamine acid, X$_2$ is Tyrosine, and one other amino acid is substituted with Alanine.

In another embodiment, the anti-Factor Bb antibodies of the invention has a light chain variable domain amino acid sequence that is at least 80% identical to a sequence selected from the group consisting of SEQ ID NO:8-11 and a heavy chain variable domain amino acid sequence that is at least 80% identical to a sequence selected from the group consisting of SEQ ID NO:12-15. In another embodiment, the anti-Factor Bb antibodies of the invention has a light chain variable domain amino acid sequence that is at least 80% identical to a sequence selected from the group consisting of SEQ ID NO:24-27 and a heavy chain variable domain amino acid sequence that is at least 80% identical to a sequence selected from the group consisting of SEQ ID NO:28-31. In another aspect, the anti-Factor Bb antibodies of the invention has a light chain variable domain amino acid sequence selected from the group consisting of SEQ ID NO:8-11 and a heavy chain variable domain amino acid sequence selected from the group consisting of SEQ ID NO:12-15. In another aspect, the anti-Factor Bb antibodies of the invention has a light chain variable domain amino acid sequence that is selected from the group consisting of SEQ ID NO:24-27 and a heavy chain variable domain amino acid sequence selected from the group consisting of SEQ ID NO:28-31. In other aspect, the anti-Factor Bb antibody of the invention has a light chain variable domain amino acid sequence of SEQ ID NO:11 and a heavy chain variable domain amino acid sequence of SEQ ID NO:15.

In another embodiment, the anti-Factor Bb antibodies of the invention comprises a heavy light chain and a light heavy chain variable domain selected from the light and heavy chain variable domain amino acid sequences: SEQ ID NO:8/SEQ ID NO:12; SEQ ID NO:8/SEQ ID NO:13; SEQ ID NO:8/SEQ ID NO:14; SEQ ID NO:8/SEQ ID NO:15; SEQ ID NO:9/SEQ ID NO:12; SEQ ID NO:9/SEQ ID NO:13; SEQ ID NO:9/SEQ ID NO:14; SEQ ID NO:9/SEQ ID NO:15; SEQ ID NO:10/SEQ ID NO:12; SEQ ID NO:10/SEQ ID NO:13; SEQ ID NO:10/SEQ ID NO:14; and SEQ ID NO:10/SEQ ID NO:15; SEQ ID NO:11/SEQ ID NO:12; SEQ ID NO:11/SEQ ID NO:13; SEQ ID NO:11/SEQ ID NO:14; and SEQ ID NO:11/SEQ ID NO:15.

In another embodiment, the anti-Factor Bb antibodies of the invention comprises a heavy light chain and a light heavy chain variable domain selected from the light and heavy chain variable domain amino acid sequences: SEQ ID NO:24/SEQ ID NO:28; SEQ ID NO:24/SEQ ID NO:29; SEQ ID NO:24/SEQ ID NO:30; SEQ ID NO:24/SEQ ID NO:31; SEQ ID NO:25/SEQ ID NO:28; SEQ ID NO:25/SEQ ID NO:29; SEQ ID NO:25/SEQ ID NO:30; SEQ ID NO:25/SEQ ID NO:31; SEQ ID NO:26/SEQ ID NO:28; SEQ ID NO:26/SEQ ID NO:29; SEQ ID NO:26/SEQ ID NO:30; and SEQ ID NO:26/SEQ ID NO:31; SEQ ID NO:27/SEQ ID NO:28; SEQ ID NO:27/SEQ ID NO:29; SEQ ID NO:27/SEQ ID NO:30; and SEQ ID NO:27/SEQ ID NO:31.

In another aspect, the anti-Factor Bb antibody of the invention is a monoclonal antibody, a polyclonal antibody, a recombinant antibody, a humanized antibody, a chimeric antibody, a multispecific antibody, or an antibody fragment. In another aspect, the anti-Factor Bb antibody of the invention is a Fab fragment, a Fab' fragment, a F(ab')$_2$ fragment, a Fv fragment, a diabody, or a single chain antibody molecule. In another aspect, the anti-Factor Bb antibody of the invention is of the IgG1, IgG2, IgG3, or IgG4 type. In another aspect, the anti-Factor Bb antibody of the invention is coupled to a labeling group. That labeling group can be an optical label, a radioisotope, a radionuclide, an enzymatic group, or a biotinyl group.

In another embodiment, the invention is a process for preparing an isolated antibody of the invention that comprises preparing the antibody of the invention form a host cell that secretes the antibody. In one aspect, this means to isolate or purify the antibody from the cell culture medium in which the host cell is grown.

In another embodiment, the invention is a nucleic acid molecule encoding an isolated antibody of the invention. In one aspect, the nucleic acid molecule encoding the antibody of the invention is operable linked to a control sequence.

In another embodiment, the invention is a pharmaceutical composition that comprises at least one antibody of the invention and a pharmaceutically acceptable carrier. In one aspect, the pharmaceutical composition may also comprise an additional active agent.

In another embodiment, the invention is a method for treating or preventing a condition in a patient in need of treatment or prevention comprising administering to said patient an effective amount of at least one anti-Factor Bb antibody of the invention and thereby treating or preventing the condition. In one aspect, the condition is an ocular disease. In another aspect, the condition is age-related macular degeneration (AMD).

DETAILED DESCRIPTION OF THE INVENTION

Figure 1:
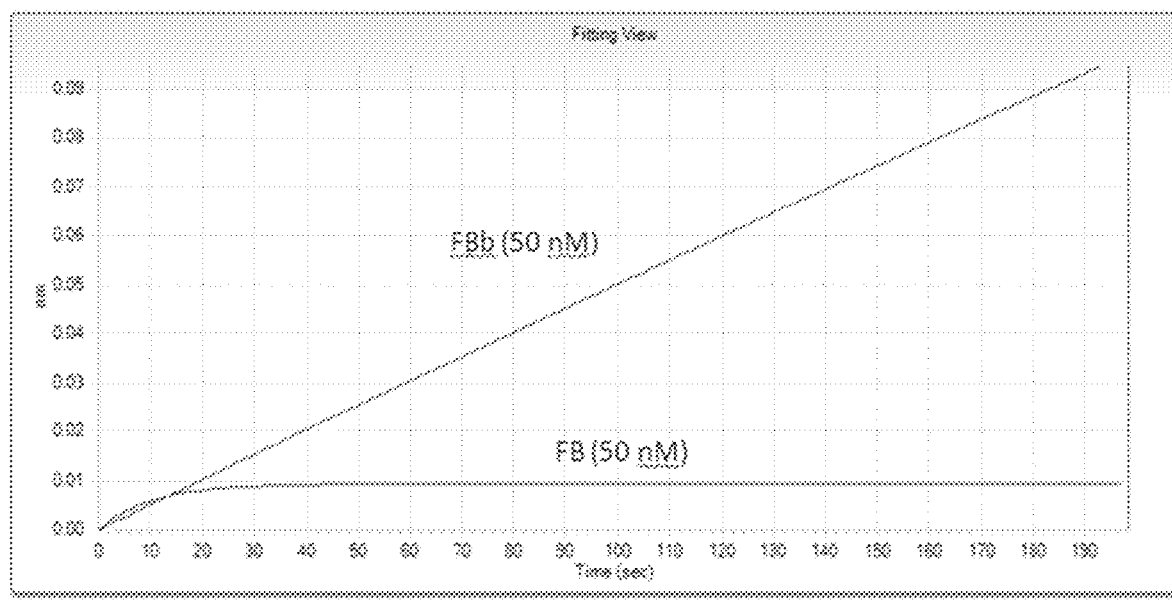
FIG. 1 depicts the binding analysis of an anti-Factor Bb monoclonal antibody, using Factor B and Factor Bb antigens in a Bio-Layer Interferometry assay.

The section headings used herein are for organizational purposes only and are not to be construed as limiting the subject matter described.

Standard techniques can be used for recombinant DNA, oligonucleotide synthesis, tissue culture and transformation, protein purification etc. Enzymatic reactions and purification techniques can be performed according to the manufacturer's specifications or as commonly accomplished in the art or as described herein. The following procedures and techniques can be generally performed according to conventional methods well known in the art and as described in various general and more specific references that are cited and discussed throughout the specification. See, e.g., Sambrook et al., 2001, *Molecular Cloning: A Laboratory Manual*, 3$^{rd}$ ed., Cold Spring Harbor Laboratory Press, Cold Spring Harbor, N.Y., which is incorporated herein by reference for any purpose. Unless specific definitions are provided, the nomenclature used in connection with, and the laboratory procedures and techniques of, molecular biology, biological chemistry, physical and bio-physical chemistry, analytical chemistry, organic chemistry, and medicinal and pharmaceutical chemistry described herein are those well known and commonly used in the art. Standard techniques can be used for chemical synthesis, chemical analyses, pharmaceutical preparation, formulation, and delivery and treatment of patients.

The following definitions are used herein:

"Protein," as used herein, is meant to refer to at least two covalently attached amino acids, and is used interchangeably with polypeptides, oligopeptides, and peptides. The two or more covalently attached amino acids are attached by a peptide bond.

"Factor B" refers to human Factor B, the amino acid sequence of which is shown in SEQ ID NO:16. Factor B, Protein B, Complement Factor B, Complement Protein B refer to the same sequence as SEQ ID NO:16. Other terms can be used to refer to the same, or variants of Factor B (for example, "preproprotein B".) Factor Ba (SEQ ID NO:17) is one polypeptide fragment of Factor B.

"Factor Bb," refers to a polypeptide fragment (SEQ ID NO:7) of human Factor.

The terms "antibody" and "immunoglobulin" are used interchangeably in the broadest sense to refer to a protein, comprising one or more polypeptide chains that interact with a specific antigen, through binding of a plurality of CDRs and an epitope of the antigen. An antibody can be a monoclonal (for e.g., full length or intact monoclonal antibodies), polyclonal, multivalent, and/or multispecific (e.g., bispecific antibodies so long as they exhibit the desired biological activity). Antibodies can also be or include antibody fragments (as described herein).

"Epitope" is used to refer to a sequence, structure, or molecule that is recognized and bound by an antibody. An epitope can be referred to as an "antigenic site."

"Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcR binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

"Monoclonal" antibody as used herein refers to an antibody obtained from a population of cells, wherein the population of cells is clonally-derived from a single parent cell. Monoclonal antibodies are homogeneous antibodies, i.e., the individual antibodies comprising the population are identical in that they are derived from the same genes and have the same amino acid sequence and protein structure except for possible naturally-occurring mutations that can be present in minor amounts and post-translational modifications that may, in some cases, be different. Monoclonal antibodies can, in some embodiments, be highly specific. In some embodiments, a monoclonal antibody can be directed against a single antigenic site. Furthermore, in contrast to other antibody preparations which typically include different antibodies directed against different determinants (epitopes), each monoclonal antibody is directed against a single determinant on the antigen. Individual monoclonal antibodies can be produced by any particular method. For example, the monoclonal antibodies to be used in accordance with the present disclosure can be made by the hybridoma method first described by Kohler et al. (1975) Nature 256:495, or can be made by recombinant DNA methods (see, e.g., U.S. Pat. No. 4,816,567), or from phage antibody libraries using the techniques described in Clackson et al. (1991) Nature 352: 624-628 and Marks et al. (1991) J. Mol. Biol. 222:581-597.

"Polyclonal" antibody is used to describe a heterogeneous population of antibodies derived from a heterogeneous population of parent, antibody-producing cells. In most cases the polyclonal antibodies have different affinity for differing epitopes and are produced from genes with differing sequences.

"Chimeric" antibodies are antibodies comprising amino acid sequences derived from two or more different species.

"Humanized" antibodies are chimeric antibodies derived from a non-human parent antibody. In many cases specific amino acid positions in a humanized antibody, have been changed to correspond to the identity of the amino acid at a corresponding position in a human antibody. In many cases, positions in a variable region of the parent (non-human) antibody are replaced with amino acids from a variable region of a human species. This creates a humanized mouse, rat, rabbit or nonhuman-primate antibody having the desired specificity, affinity, and capacity.

"Variant" refers to sequences that comprise at least one difference compared to a parent sequence. A variant polypeptide is a protein having at least about 75% amino acid sequence identity to a parent sequence. A variant protein can have at least about 80% amino acid sequence identity, or at least about 85% amino acid sequence identity, or at least about 90% amino acid sequence identity, or at least about 95% amino acid sequence identity, or at least about 98% amino acid sequence identity, or at least about 99% amino acid sequence identity with a native, or wild-type amino acid sequence. In some cases variant antibodies are antibodies having one or more difference(s) in amino acid sequence as compared to a parent antibody. Humanized and chimeric antibodies are variant antibodies. Variant antibodies, therefore, comprise less than 100% sequence identity with a parent antibody.

"Isolated" or "purified" refers to a molecule that has been separated and/or recovered from at least one component of its natural environment, wherein the component is a material that can interfere with the use, or activity, of the molecule. Components include peptides, sugars, nucleic acids, enzymes, hormones, and other proteinaceous or nonproteinaceous solutes.

"Complementarity Determining Regions" (CDRs) refers to one or more regions within an antibody wherein the residues of one or more CDR aid in antigen binding. In many cases, individual amino acids of the CDRs can be in close proximity to atoms of the target antigen. In some embodiments the CDR may be located in an immunoglobulin that may be comprised of three CDR regions. In some cases, as where there is more than one CDR sequence in a larger amino acid sequence, the CDRs may be separated by other sequences, and the CDRs numbered. In some cases, multiple CDRs are identified as CDR1, CDR2 and CDR3. Each CDR may comprise amino acid residues from a Complementarity Determining Region as defined by Kabat. Kabat et al., Sequences of Proteins of Immunological Interest, 5th Ed. Public Health Service, National Institutes of Health, Bethesda, Md. (1991)). Amino acid numbering of CDRs, as well as other sequences within an antibody, or antibody fragment is according to that of Kabat. In many cases, CDRs can be defined by their position in a variable region sequence (numbering as in Kabat), for example the light chain CDR 1 may comprise the amino acid sequence between position 24 and position 33; between position 50 and position 56 for LC CDR2; and between position 89 and position 97 for LC CDR 3; and the heavy chain CDRs may lie between position 26 and position 33 for CDR1; position 50 and position 66 for HC CDR 2; and between position 97 and position 103 for HC CDR 3, and/or hypervariable loops may lie between light chain residues 26-32 (LC CDR1), residues 50-52 (LC CDR2) and residues 91-96 (LC CDR3); and heavy chain residues 26-32 (HC CDR1), residues 53-55 (HC CDR2) and residues 97-101 (HC CDR3). In some instances, a Complementarity Determining Region can include amino acids from both a CDR region defined according to Kabat and a hypervariable loop. In some embodiments, as in where the antibody is a single chain immunoglobulin, there may be more than one CDR, more than two CDRs, more than three CDRs, more than four CDRs, or more than five CDRs. In some embodiments, an antibody may be comprised of six CDRs.

"Framework regions," FRs, are variable domain residues other than the CDR residues. In most embodiments a variable domain has between two and four FRs identified sequentially. For example a variable region comprising three CDRs, has four FRs: FR1, FR2, FR3 and FR4. Where the CDRs are defined according to Kabat, the light chain FR residues are positioned at about residues 1-23 (LCFR1), 34-49 (LCFR2), 57-88 (LCFR3), and 98-107 (LCFR4) and the heavy chain FR residues are positioned about at residues 1-25 (HCFR1), 34-49 (HCFR2), 67-96 (HCFR3), and 104-113 (HCFR4) in the heavy chain residues. If the CDRs comprise amino acid residues from hypervariable loops, the light chain FR residues are positioned about at residues 1-23 (LCFR1), 34-49 (LCFR2), 57-88 (LCFR3), and 98-107 (LCFR4) in the light chain and the heavy chain FR residues are positioned about at residues 1-25 (HCFR1), 34-49 (HCFR2), 67-96 (HCFR3), and 104-113 (HCFR4) in the heavy chain residues. In some instances, when the CDR comprises amino acids from both a CDR as defined by Kabat and those of a hypervariable loop, the FR residues will be adjusted accordingly. For example, when HC CDR1 includes amino acids H26-H35, the heavy chain FR1 residues are at positions 1-25 and the FR2 residues are at positions 36-49.

"Variable domain" refers to portions of a light chain and a heavy chain of traditional antibody molecule that includes amino acid sequences of Complementarity Determining Regions (CDRs), and Framework Regions (FRs). VH refers to the variable domain of the heavy chain. VL refers to the variable domain of the light chain.

"Fv" or "Fv fragment" refers to an antibody fragment which contains a complete antigen recognition and binding site, comprising the FR and CDR sequences. In many embodiments, the Fv consists of a dimer of one heavy and one light chain variable domain in tight association, which can be covalent in nature, for example in a single chain Fv molecule (scFv). The three CDRs of each variable domain interact to define an antigen binding site on the surface of the VH-VL polypeptide. Collectively, the six CDRs or a subset thereof confer antigen binding specificity to the antibody. However, even a single variable domain (or half of an Fv comprising only three CDRs specific for an antigen) has, in some cases, the ability to recognize and bind antigen, although usually at a lower affinity than the entire binding site.

"Fab" or "Fab fragment" contains a variable and constant domain (CL) of the light chain and a variable domain and the first constant domain (CH1) of the heavy chain. F(ab')$_2$ antibody fragments comprise a pair of Fab fragments which are generally covalently linked near their carboxy termini by hinge cysteines between them. Other chemical couplings of antibody fragments are also known in the art.

"Percent (%) amino acid sequence identity" is defined as the percentage of amino acid residues in a candidate sequence that are identical with the amino acid residues in a reference sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

"Percent (%) amino acid sequence homology" is defined as the percentage of amino acid residues in a candidate sequence that are homologous with the amino acid residues in a reference sequence, after aligning the sequences and introducing gaps, if necessary, to achieve the maximum percent sequence homology. This method takes into account conservative substitutions. Conservative substitutions are those substitutions that allow an amino acid to be substituted with a similar amino acid. Amino acids can be similar in several characteristics, for example, size, shape, hydrophobicity, hydrophilicity, charge, isoelectric point, polarity, aromaticity, etc. Alignment for purposes of determining percent amino acid sequence homology can be achieved in various ways that are within the ordinary skill of those persons of skill in the art. In some cases, amino acid sequences can be aligned using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence homology is then calculated relative to the longer sequence, i.e. even if a shorter sequence shows 100% sequence identity with a portion of a longer sequence, the overall sequence identity will be less than 100%.

"Percent (%) nucleic acid sequence identity" is defined as the percentage of nucleotides in a candidate sequence that are identical with the nucleotides in a reference sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. Sequence identity is then calculated relative to the longer sequence, i.e. even if a shorter sequence shows 100% sequence identity with a portion of a longer sequence, the overall sequence identity will be less than 100%.

"Activity" or "biological activity" of a molecule can depend upon the type of molecule and the availability of tests for assaying a given activity. For example, in the context of a Factor Bb antibody, activity refers to its ability to partially or fully inhibit a biological activity of Factor Bb, for example, binding to other complement proteins, serine protease activity, or MAC formation. A preferred biological activity of the claimed Factor Bb antibody is the ability to achieve a measurable improvement in the state, e.g. pathology, of a factor Bb-associated disease or condition, such as, for example, a complement-associated eye condition. In some cases, the activity inhibited by the disclosed anti-Factor Bb antibody is Factor Bb protease or cleavage activity. In other cases the activity is the ability to bind other complement proteins in a complex. In some embodiments, the activity of the disclosed anti-Factor Bb antibody is measured by its ability to inhibit hemolysis. The activity can be determined through the use of in vitro or in vivo tests, including binding assays, using a relevant animal model, or human clinical trials.

"Complement-associated eye condition" is used in the broadest sense and includes all eye conditions the pathology of which involves complement, activated by either the classical, lectin, alternative or extrinsic pathways. Complement-associated eye conditions include, without limitation, macular degenerative diseases, such as all stages of age-related macular degeneration (AMD), including dry and exudative (non-exudative and exudative) forms, choroidal neovascularization (CNV), uveitis, diabetic and other ischemia-related retinopathies including diabetic macular edema, Central Retinal Vein Occlusion (CRVO), Branched Retinal Vein Occlusion (BRVO), and other intraocular neovascular diseases, such as diabetic macular edema, pathological myopia, von Hippel-Lindau disease, histoplasmosis of the eye, corneal neovascularization, and retinal neovascularization. A preferred group of complement-associated eye conditions includes age-related macular degeneration (AMD), including dry and wet (non-exudative and exudative) AMD, choroidal neovascularization (CNV), Macular Telangiectasia, uveitis, diabetic and other ischemia-related neovascular-related retinopathies, or cellular degenerative diabetic macular edema, pathological myopia, von Hippel-Lindau disease, histoplasmosis of the eye, Doyne honeycomb retinal dystrophy/Malattia Leventinese, Stargarts disease, Glucoma, Central Retinal Vein Occlusion (CRVO), BRVO, corneal neovascularization, retinal neovascularization.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound that possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N methylglucamine, and the like. In certain embodiments, a pharmaceutically acceptable salt is the hydrochloride salt. In certain embodiments, a pharmaceutically acceptable salt is the sodium salt.

"Pharmaceutically acceptable excipient" refers to a pharmaceutically acceptable diluent, a pharmaceutically acceptable adjuvant, a pharmaceutically acceptable vehicle, a pharmaceutically acceptable carrier, or a combination of any of the foregoing with which a compound provided by the present disclosure can be administered to a patient, which does not destroy the pharmacological activity thereof and which is non-toxic when administered in doses sufficient to provide a therapeutically effective amount of the compound or a pharmacologically active metabolite thereof.

"Treatment" is an administration of at least one therapeutic agent for preventing the development or altering the pathology of a disorder, or alleviating or lessening a symptom of a disorder. Accordingly, treatment refers to both therapeutic treatment and prophylactic or preventative measures. Those in need of treatment include those already with the disorder as well as those in which the disorder is to be prevented. As disclosed herein, the preferred agent for administration comprises at least one of the disclosed anti-Factor Bb antibodies. In treatment of a complement related disease, the therapeutic agent, comprising at least one of the presently disclosed antibodies or a coding sequence for such antibody, may directly or indirectly alter the magnitude of response of a component of the complement pathway, or render the disease more susceptible to treatment by other therapeutic agents, e.g., antibiotics, antifungals, anti-inflammatory agents, chemotherapeutics, etc.

"Therapeutically effective amount" refers to the amount of an agent that, when administered to a subject for treating a disease, or at least one of the clinical symptoms of a disease, is sufficient to effect such treatment of the disease or symptom thereof. The specific therapeutically effective amount may vary depending, for example, on the agent, the disease and/or symptoms of the disease, severity of the disease and/or symptoms of the disease, the age, weight, and/or health of the patient to be treated, and the judgment of the prescribing physician. An appropriate amount in any given compound can be ascertained by those skilled in the art and/or is capable of determination by routine experimentation.

"Therapeutically effective dose" refers to a dose that provides effective treatment of a disease in a patient. A therapeutically effective dose may vary from agent to agent and/or from patient to patient, and may depend upon factors such as the condition of the patient and the severity of the disease. A therapeutically effective dose can be determined in accordance with routine pharmacological procedures known to those skilled in the art.

"Pathology" of a disease, such as a complement-associated eye condition, includes all phenomena that compromise the well-being of the patient. This includes, without limitation, abnormal or uncontrollable cell growth, protein production, abnormal or uncontrollable cell death, auto-antibody production, complement production, complement activation, MAC formation, interference with the normal functioning of neighboring cells, release of cytokines or other secretory products at abnormal levels, suppression or aggravation of any inflammatory or immunological response, infiltration of inflammatory cells into cellular spaces, etc.

"Mammal" as used herein refers to any animal classified as a mammal, including, without limitation, humans, higher primates, domestic and farm animals, and zoo, sports or pet animals such horses, pigs, cattle, dogs, cats and ferrets, etc. In a preferred embodiment of the invention, the mammal is a human.

Administration "in combination with" one or more further therapeutic agents includes simultaneous (concurrent) and consecutive administration in any order.

The present disclosure provides antibodies that bind Factor Bb protein.

The antibodies described herein comprise a scaffold structure with one or more Complementarity Determining Regions (CDRs). In certain embodiments, the CDRs include no more than two amino acid additions, deletions, or substitutions from one or more of the heavy chain CDR1, CDR2, and CDR3, and the light chain CDR1, CDR2 and CDR3 of a parent sequence. In other embodiments, the CDRs are defined by a consensus sequence having common conserved amino acid sequences and variable amino acid sequences as described herein.

In certain embodiments, the scaffold structure of the Factor Bb antibodies of the disclosure can be based on antibodies, including, but not limited to, monoclonal antibodies, bispecific antibodies, minibodies, domain antibodies, synthetic antibodies (e.g. antibody mimetics), chimeric antibodies, humanized antibodies, antibody fusions (e.g. antibody conjugates), and fragments of each, respectively. The various structures are further described and defined hereinbelow. The Factor Bb antibodies are useful in treating consequences, symptoms, and/or the pathology associated with Factor Bb activity. These include, but are not limited to, atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Bane syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation leukopheresis, plasmapheresis, heparin-induced extracorporeal membrane oxygenation LDL precipitation, extracorporeal membrane oxygenation and the like.

Other uses for the disclosed antibodies include, for example, diagnosis of complement- and Factor Bb-associated diseases.

Aspects of the present disclosure provide Factor Bb antibodies, particularly antibodies that include at least one CDR including heavy and/or light CDRs, as more fully described below, or combinations thereof.

In one aspect, the Factor Bb antibodies inhibit activity of Factor Bb, or inhibit the ability of Factor Bb to form protein complexes. Without being held to a particular mechanism or theory, in some embodiments the antibodies interrupt the complement pathway, thereby interrupting the complement cascade, formation of the MAC, and cell lysis. This disruption may include, but is not limited to dry and wet (non-exudative and exudative) AMD, choroidal neovascularization (CNV), uveitis, diabetic and other ischemia-related retinopathies, diabetic macular edema, pathological myopia, von Hippel-Lindau disease, histoplasmosis of the eye, Central Retinal Vein Occlusion (CRVO), corneal neovascularization, retinal neovascularization, and the like.

The antibodies of the disclosure thus may serve to identify conditions related to the complement system or Factor Bb related diseases or conditions. In addition, the antibodies can be used to regulate and/or suppress effects mediated by Factor B and/or other, downstream, complement proteins, as such having efficacy in the treatment and prevention of various diseases or conditions associated with complement and/or Factor Bb. This disruption may include, but is not limited to atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Bane syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation leukopheresis, plasmapheresis, heparin-induced extracorporeal membrane oxygenation LDL precipitation, extracorporeal membrane oxygenation, and the like.

More specifically, the disclosure provides anti-Factor Bb antibodies and polynucleotides that encode them. In various aspects, the anti-Factor Bb antibodies inhibit at least one of the biological responses mediated by the Factor Bb and/or other complement proteins, and as such can be useful for ameliorating the effects of complement-associated and Factor Bb-associated diseases or disorders. Also provided by the disclosure are expression systems, including mammalian cell lines and bacterial cells, for the production of Factor Bb antibodies and methods of treating diseases associated with Factor Bb.

The antibodies of the present disclosure comprise a scaffold structure and one or more complementary determining regions (CDRs) that bind to Factor Bb. In one embodiment, an amino acid sequence comprises any of SEQ ID NOs:1-6 or SEQ ID NOs: 18-23.

In various embodiments, the antibody comprises a first and/or second amino acid sequence. In an embodiment, the first and/or the second amino acid sequence is selected from the group consisting of SEQ ID NOs:8-15 or SEQ ID NOs: 24-31.

In various embodiments, the antibodies can include one or both of the first and second amino acid sequences. The first and second amino acid sequences can be a single linear amino acid sequence, can be covalently bonded by disulfide bridges, or can be non-covalently bonded.

Factor Bb

Complement factor B is a glycosylated protein composed of a single 93,000 Da polypeptide chain encoded by the CFB gene. It is an essential component of the alternative pathway of complement activation and is found in human plasma at approximately 200 µg/mL. In the presence of Mg$^+$ factor B binds to C3b and the C3b:B complex can be activated by factor D, a serine protease that circulates as an active trypsin-like serine protease. Cleavage of factor B by factor D causes the release of the Ba fragment (33,000 Da) and leaves the (60,000 Da) Bb fragment bound to C3b. This Bb subunit is a serine protease, called a C3 and a C5 convertase because it converts both of these proteins to their active forms by cleaving off the small peptides C3a and C5a, respectively.

Factor B is a tightly regulated, highly specific serine protease. In its activated form, it catalyzes the central amplification step of complement activation to initiate inflammatory responses, cell lysis, phagocytosis and B-cell stimulation. Factor B is activated through assembly with either surface-bound C3b, or its soluble counterpart C3($H_2O$). After binding to C3, Factor B is cleaved by factor D into a small fragment, Factor Ba (residues 1-234) and a large fragment, Factor Bb (residues 235-739). Factor Ba dissociates from the complex, leaving behind the alternative pathway C3 convertase complex C3b-Bb, which cleaves C3 into C3a and C3b. The C3b-Bb protease complex is not stable, and once dissociated from the complex Factor Bb does not re-associate with C3b.

The proenzyme factor B consists of three N-terminal complement control protein (CCP) domains, connected by a 45-residue linker to a VWA domain and a C-terminal serine protease (SP) domain, which carries the catalytic center. Striking differences from other serine proteases are observed in the active center of factor B. Factor Bb comprises the C-terminal serine protease domain, and the CCP domains are found in Factor Ba.

The amino acid sequence of the human Factor B is shown in SEQ ID NO:16. Other forms of Factor B that are useful in the present disclosure include mutants and variations that are at least 70% or at least 90% homologous to the human native Factor B sequence of SEQ ID NO:16.

The amino acid sequence of human Factor Bb is SEQ ID NO:7. Other forms of Factor Bb that are useful in the present disclosure include mutants and variations that are at least 70% or at least 90% homologous to the native Factor Bb sequence of SEQ ID NO:7.

The amino acid sequence of human Factor Ba is SEQ ID NO:17. Other forms of Factor Ba that are useful in the present disclosure include mutants and variations that are at least 70% or at least 90% homologous to the native Factor Ba sequence of SEQ ID NO:17.

Inhibiting Factor B, Factor Bb, or Factor Ba function/activity as described herein represents inhibition of Factor Bb. One example of assaying the complement alternative pathway is the Hemolysis Assay: Activation of the alternative pathway of (AP) requires higher concentrations of serum than the classical pathway. Generally, a final concentration of 5 mM Mg++ in the presence of 5 mM EGTA is used in the assays where the EGTA chelates Ca++ preferentially. The AP of most mammalian species is activated spontaneously by rabbit erythrocytes so they are a convenient target. Prepare rabbit erythrocytes (Complement Technology, Inc.) by washing 3 times with GVB0 (CompTech® product) and resuspending into 5×108/ml. Different amount of anti-factor Bb antibody was diluted with GVB0. Mix the 100 ul reaction on ice in the order of serial diluted anti-factor Bb antibody, 0.1M MgEGTA (CompTech® product), 1/2NHS (normal human serum diluted 1/2 with GVB0), and rabbit Er. Then, incubate the reaction at 37° C. for 30 minutes on a shaker. Add 1.0 ml cold GVBE. Mix and centrifuge for 3 min at approx. 1000×g, or higher, to pellet cells. Transfer 100 ul of the supernatant to a 96-well plate and read at 412 nm (Pro SoftMax® Pro 4.7.1). Data was analyzed using GraphPad Prism 6.

Factor Bb Antibodies.

In one aspect, the disclosure provides antibodies that bind Factor Bb with greater affinity than they bind Factor B.

In certain aspects, the disclosure provides recombinant antibodies that bind Factor Bb, i.e. Factor Bb antibodies or anti-Factor Bb antibodies. In this context, recombinant antibodies can be produced using recombinant techniques, i.e., through the expression of a recombinant nucleic acid as described below. Methods and techniques for the production of recombinant proteins are well known in the art.

In some embodiments, the antibodies of the disclosure are isolated or purified. An isolated or purified antibody can be unaccompanied by at least some of the material with which it is normally associated in its natural state (contaminating material). In a preferred embodiment, the contaminating material constitutes less than about 50%, more preferably less than about 20%, and more preferably less than about 10% by weight of the total weight of a given sample. In some embodiments the contaminant may be a protein or peptide.

A pure protein comprises at least about 50% by weight of the total protein, with at least about 80% being preferred, and at least about 90% being particularly preferred. In many embodiments, the purified anti-Factor Bb antibody is produced from in or from an organism other than the organism from which it is derived. In some embodiments, the anti-Factor Bb antibody can be made at a significantly higher concentration than is normally seen, through the use of an inducible promoter or high expression promoter, such that the antibody is made at increased concentration levels.

In some embodiments, the isolated or purified antibody can be removed from components that can interfere with diagnostic and/or therapeutic uses for the antibody. In preferred embodiments, the antibody will be purified to greater than 90% by weight of antibody as determined by the Lowry method, and most preferably more than 99% by weight, to a degree sufficient to obtain at least 15 residues of N-terminal or internal amino acid sequence by use of a common amino acid sequencing technique (e.g. Edman degradation and mass spectrometry), or to homogeneity by SDS-PAGE under reducing or nonreducing conditions using Coomassie blue or silver stain. Isolated antibodies include antibodies in situ within recombinant cells since at least one component of the antibody's natural environment will not be present. Ordinarily, however, isolated antibody will be prepared by at least one purification step.

The disclosed antibody can bind specifically to Factor Bb and can be used to inhibit or modulate the biological activity of Factor Bb. In certain embodiments, the disclosed antibodies are created by immunization of an animal, in other cases antibodies can be produced by recombinant DNA techniques. In additional embodiments, anti-Factor Bb antibodies can be produced by enzymatic or chemical cleavage of naturally occurring antibodies. In some embodiments, the antibody can comprise a tetramer. In some of these embodiments, each tetramer is typically composed of two identical pairs of polypeptide chains, each pair having one light chain (typically having a molecular weight of about 25 kDa) and one heavy chain (typically having a molecular weight of about 50-70 kDa). The amino-terminal portion of each chain includes a variable region of about 100 to 110 or more amino acids and can be responsible for antigen recognition. The carboxy-terminal portion of each chain can define a constant region, which is primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4.

Some naturally occurring antibodies, for example antibodies found in camels and llamas, can be dimers consisting of two heavy chains and include no light chains. Muldermans et al., 2001, *J. Biotechnol.* 74:277-302; Desmyter et al., 2001, *J. Biol. Chem.* 276:26285-26290. Crystallographic studies of camel antibodies have revealed that the CDR3 regions of these antibodies form a surface that interacts with the antigen and thus is critical for antigen binding like in the more typical tetrameric antibodies. The disclosure encompasses dimeric antibodies consisting of two heavy chains, or fragments thereof that can bind to and/or inhibit the biological activity of Factor Bb.

The antibodies of the disclosure specifically bind to a Factor Bb protein, preferably a human Factor Bb. An antibody can specifically bind to a target antigen, when the antibody has a higher binding affinity for that target antigen than for any other antigen or protein. Thus, the antibodies described herein bind with higher affinity to Factor Bb, than to any other protein. Typically, the binding affinity is measure by determining an equilibrium binding constant, for example a $K_d$ (or Kd), or $K_a$ (or Ka). In some embodiments the disclosed antibody binds to a target antigen with a Kd from about $10^{-7}$ M to about $10^{-12}$ M, or from about $10^{-8}$ M to about $10^{-11}$ M, or from about $10^{-9}$ M to about $10^{-10}$ M. In most cases, the Kd of the disclosed antibody for the a non-target antigen can be higher than the Kd for the target antigen, for example where the Kd for the target is $10^{-10}$ M and the Kd for the non-target is $10^{-8}$ M In some cases the Kd for the other antigen is greater than 1× the target antigen Kd, greater than 2× the target antigen Kd, greater than 3× the target antigen Kd, greater than 4× the target antigen Kd, greater than 5× the target antigen Kd, greater than 6× the target antigen Kd, greater than 7× the target antigen Kd, greater than 8× the target antigen Kd, greater than 9× the target antigen Kd, greater than 10× the target antigen Kd (for example where the Kd of the antibody is $X^{-09}$ M for the target antigen, the Kd of the antibody for another antigen can be 10× greater, or $X^{-08}$ M), or greater than 100× (for example where the Kd of the antibody is $X^{-10}$ M for the target antigen, the Kd of the antibody for another antigen can be 10× greater, or $X^{-08}$ M). In some cases, the equilibrium binding constant can be expressed as an equilibrium association constant, $K_a$ or Ka.

The equilibrium binding constant, can be determined using various methods. In some cases, an equilibrium binding constant for the disclosed antibody is determined by measuring on ($k_1$) and off ($k_{-1}$) rates in a protein binding assay. One exemplary method of determining the equilibrium binding constant is by Bio-Layer Interferometry BLI is a label-free technology capable of determining binding kinetics in solution. In one exemplary method, an antibody can be a human IgG, and the antibody can be captured by an Anti-human IgG Fc capture (AHC) biosensor tips (FortéBio, Menlo Park, Calif., USA) according to the manufacturer's directions. Other types of protein binding assays include: Co-immunoprecipitation; Bimolecular fluorescence complementation; Affinity electrophoresis; Pull-down assays; Label transfer; The yeast two-hybrid screen; Phage display; in vivo crosslinking of protein complexes using photo-reactive amino acid analogs; Tandem affinity purification; Chemical cross-linking; Chemical cross-linking followed by high mass MALDI mass spectrometry; SPINE (Strepprotein interaction experiment); Quantitative immunoprecipitation combined with knock-down; Proximity ligation assay Bio-Layer Interferometry; Dual polarisation interferometry; Static light scattering; Dynamic light scattering; Surface plasmon resonance; Fluorescence polarization/anisotropy; fluorescence correlation spectroscopy; Fluorescence resonance energy transfer; Protein activity determination by NMR multi-nuclear relaxation measurements, or 2D-FT NMR spectroscopy in solutions, combined with nonlinear regression analysis of NMR relaxation or 2D-FT spectroscopy data sets; Protein-protein docking; Isothermal Titration Calorimetry; and, Microscale Thermophoresis.

In embodiments where the antibody is used for therapeutic applications, one characteristic of a Factor Bb antibody is that it can modulate and/or inhibit one or more biological activities of, or mediated by, Factor Bb. In this case, an antibody can bind specifically to Factor Bb, can substantially modulate the activity of Factor Bb, and/or can inhibit the binding of Factor Bb to other proteins (e.g. Factor C3). In some cases, the antibody may inhibit the serine protease activity of Factor Bb by at least about 20%, 40%, 60%, 80%, 85%, or more.

In many embodiments, Factor Bb activity, and the antibody's ability to inhibit that activity, is measured by analyzing lysis of red blood cells in the presence of 10% human serum. Activation of the alternative pathway of (AP) requires higher concentrations of serum than the classical pathway. Generally, a final concentration of 5 mM $Mg^{++}$ in the presence of 5 mM EGTA is used in the assays where the EGTA chelates $Ca^{++}$ preferentially. The AP of most mammalian species is activated spontaneously by rabbit erythrocytes so they are a convenient target. Prepare rabbit erythrocytes (Complement Technology, Inc.) by washing 3 times with GVB0 (CompTech® product) and re-suspending into $5 \times 10^8$/ml. Different amount of anti-factor Bb antibody was diluted with GVB0. Mix the 100 ul reaction on ice in the order of serial diluted anti-factor Bb antibody, 0.1M MgEGTA (CompTech® product), 1/2NHS (normal human serum diluted 1/2 with GVB0), and rabbit Er. Then, incubate the reaction at 37° C. for 30 minutes on a shaker. Add 1.0 ml cold GVBE. Mix and centrifuge for 3 min. at approx. 1000×g, or higher, to pellet cells. Transfer 100 ul of the supernatant to a 96-well plate and read at 412 nm (SoftMax® Pro 4.7.1). Data was analyzed using GraphPad Prism 6.

Not every antibody that specifically binds to an antigen can block antigen binding to its normal ligand and thus inhibit or modulate the biological effects of the antigen. As is known in the art, such an effect can depend on what portion of the antigen the antibody binds to, and on both the absolute and the relative concentrations of the antigen and the antibody, in this case, a Factor Bb antibody. To be considered capable of inhibiting or modulating the biological activity of Factor Bb, as meant herein, an antibody can be able, for example, to inhibit the serine protease activity of Factor Bb or human serum mediated hemolysis by at least about 20%, 40%, 60%, 80%, 85%, 90%, 95%, 99%, or more.

The concentration of an antibody required to inhibit Factor Bb activity can vary widely and may depend upon how tightly the antibody binds to Factor Bb. For example, one molecule or less of an antibody per molecule of Factor Bb can be sufficient to inhibit biological activity. In some embodiments, a ratio of Factor Bb antibody of about 1,000:1 to about 1:1,000, including about 2:1, 1:1, 1:2, 1:4, 1:6, 1:8, 1:10, 1:20, 1:40, 1:60, 1:100, 1:500, 1:1,000 or more can be required to inhibit the biological activity of Factor Bb. In many cases, the ability to inhibit Factor Bb activity may depend upon the concentration of Factor Bb and/or the concentration of Factor Bb antibody.

In some embodiments, the antibodies of the disclosure comprise (a) a scaffold, and (b) one or a plurality of CDRs, regions that are determinative to antigen binding specificity and affinity. Complementary Determining Regions or CDRs, are regions of an antibody that constitutes the major surface contact points for antigen binding. One or more CDRs are embedded in the scaffold structure of the antibody. The scaffold structure of the antibodies of the disclosure can be the framework of an antibody, or fragment or variant thereof, or can be completely synthetic in nature. The various scaffold structures of the antibodies of the disclosure are further described herein.

In a preferred embodiment of the presently disclosed antibodies, the antibody can be a variant antibody having an amino acid sequence with at least 75% amino acid sequence identity or similarity with the amino acid sequence of a parent antibody. For example, in some embodiments the heavy or light chain variable domain sequence of the variant antibody is 75% identical to the heavy or light chain variable domain sequence of the parent antibody, more preferably at least 80%, more preferably at least 85%, more preferably at least 90%, and most preferably at least 95%. In most cases, the variant antibody will have few or no changes in the CDR sequence, and therefore, in most cases, will bind the target antigen with a similar affinity. Identity or similarity with respect to this sequence is defined herein as the percentage of amino acid residues in the variant sequence that are identical (i.e. same residue) or similar (i.e. amino acid residue from the same group based on common side-chain properties, see below) with the parent antibody amino acid sequence, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

CDRs

The antibodies of the disclosure include scaffold regions and one or more CDRs. An antibody of the disclosure may have between one and six CDRs (as typically do naturally occurring antibodies), for example, one heavy chain CDR1 ("HC CDR1" or "HC CDR1"), and/or one heavy chain CDR2 ("HC CDR2" or "HC CDR2"), and/or one heavy chain CDR3 ("HC CDR3" or "HC CDR3"), and/or one light chain CDR1 ("LC CDR1" or "LC CDR1"), and/or one light chain CDR2 ("LC CDR2" or "LC CDR2"), and/or one light chain CDR3 ("LC CDR3" or "LC CDR3"). The term "naturally occurring" as used throughout the specification in connection with biological materials such as polypeptides, nucleic acids, host cells, and the like, refers to materials which are found in nature. In naturally occurring antibodies, a heavy chain CDR1 typically comprises about five (5) to about seven (7) amino acids, a heavy chain CDR2 typically comprises about sixteen (16) to about nineteen (19) amino acids, and a heavy chain CDR3 typically comprises about three (3) to about twenty five (25) amino acids. CDR1 of the light chain typically comprises about ten (10) to about seventeen (17) amino acids, the light chain CDR2 typically comprises about seven (7) amino acids, and the light chain CDR3 typically comprises about seven (7) to about ten (10) amino acids.

Amino acids of the present disclosure include natural and synthetic amino acids (e.g., homophenylalanine, citrulline, ornithine, and norleucine). Such synthetic amino acids can be incorporated, in particular when the antibody is synthesized in vitro by conventional methods well known in the art. In addition, any combination of peptidomimetic, synthetic and naturally occurring residues/structures can be used. Amino acid includes imino acid residues such as proline and hydroxyproline. The amino acid "R group" or "side chain" can be in either the (L)- or the (S)-configuration. In a specific embodiment, the amino acids are in the (L)- or (S)-configuration. In some embodiments, the amino acids can form peptidomimetic structures, i.e., peptide or protein analogs, such as peptoids (see, Simon et al., 1992, Proc. Natl. Acad. Sci. U.S.A. 89:9367, incorporated by reference herein), which can be resistant to proteases or other physiological and/or storage conditions.

The structure and properties of CDRs within a naturally occurring antibody are described further below. Briefly, in a traditional antibody scaffold, the CDRs are embedded within a framework in the heavy and light chain variable region where they constitute the regions responsible for antigen binding and recognition. A variable region comprises at least three heavy or light chain CDRs, (Kabat et al., 1991, Sequences of Proteins of Immunological Interest, Public Health Service N.I.H., Bethesda, Md.; see also Chothia and Lesk, 1987, J. Mol. Biol. 196:901-917; Chothia et al., 1989, Nature 342: 877-883), within a framework region (designated framework regions 1-4, FR1, FR2, FR3, and FR4, by Kabat et al., 1991; see also Chothia and Lesk, 1987). The CDRs provided by the present disclosure, however, may not only be used to define the antigen binding domain of a traditional antibody structure, but can be embedded in a variety of other scaffold structures, as described herein.

Alanine Scanning was used to identify amino acid positions in the CDR sequences that, when modified, alter the binding affinity of anti-Factor Bb antibodies.

Specific CDRs for use in the disclosed antibodies are presented in Table 1, underlined amino acids are those where substitution to alanine substantially decreased binding.

TABLE 1

| | | |
|---|---|---|
| $HC_A$ CDR1 | GDIFSSHW | SEQ ID NO: 1 |
| $HC_A$ CDR2 | EILPRSGITHYNENFNG | SEQ ID NO: 2 |
| $HC_A$ CDR3 | AINWEDS | SEQ ID NO: 3 |
| $LC_A$ CDR1 | HASQNVNVWL | SEQ ID NO: 4 |
| $LC_A$ CDR2 | KASNLHT | SEQ ID NO: 5 |
| $LC_A$ CDR3 | QQGQSYPYT | SEQ ID NO: 6 |
| $HC_B$ CDR1 | DYYMS | SEQ ID NO: 18 |
| $HC_B$ CDR2 | FSRHRVYGYTPEYSASVKG | SEQ ID NO: 19 |
| $HC_B$ CDR3 | DNPGYYAMDY | SEQ ID NO: 20 |

TABLE 1-continued

| | | |
|---|---|---|
| $LC_B$ CDR1 | KASQSVDYDGDSYMN | SEQ ID NO: 21 |
| $LC_B$ CDR2 | AASNLES | SEQ ID NO: 22 |
| $LC_B$ CDR3 | QQSNADPYT | SEQ ID NO: 23 |

The sequences for Factor B, Factor Ba and Factor Bb are shown in Table 2.

TABLE 2

Factor Bb (SEQ ID NO: 7)
KIVLDPSGSMNIYLVLDGSDSIGASNFTGAKKCLVNLIEKVASYGVKPRY
GLVTYATYPKIWVKVSEADSSNADWVTKQLNEINYEDHKLKSGTNTKKAL
QAVYSMMSWPDDVPPEGWNRTRHVIILMTDGLHNMGGDPITVIDEIRDLL
YIGKDRKNPREDYLDVYVFGVGPLVNQVNINALASKKDNEQHVFKVKDME
NLEDVFYQMIDESQSLSLCGMVWEHRKGTDYHKQPWQAKISVIRPSKGHE
SCMGAVVSEYFVLTAAHCFTVDDKEHSIKVSVGGEKRDLEIEVVLFHPNY
NINGKKEAGIPEFYDYDVALIKLKNKLKYGQTIRPICLPCTEGTTRALRL
PPTTTCQQQKEELLPAQDIKALFVSEEEKKLTRKEVYIKNGDKKGSCERD
AQYAPGYDKVKDISEVVTPRFLCTGGVSPYADPNTCRGDSGGPLIVHKRS
RFIQVGVISWGVVDVCKNQKRQKQVPAHARDFHINLFQVLPWLKEKLQDE
DLGFL Factor B (SEQ ID NO: 16)
signal peptide underlined
MGSNLSPQLCLMPFILGLLSGGVTT
TPWSLARPQGSCSLEGVEIKGGSFRLLQEGQALEYVCPSGFYPYPVQTRT
CRSTGSWSTLKTQDQKTVRKAECRAIHCPRPHDFENGEYWPRSPYYNVSD
EISFHCYDGYTLRGSANRTCQVNGRWSGQTAICDNGAGYCSNPGIPIGTR
KVGSQYRLEDSVTYHCSRGLTLRGSQRRTCQEGGSWSGTEPSCQDSFMYD
TPQEVAEAFLSSLTETIEGVDAEDGHGPGEQQKRKIVLDPSGSMNIYLVL
DGSDSIGASNFTGAKKCLVNLIEKVASYGVKPRYGLVTYATYPKIWVKVS
EADSSNADWVTKQLNEINYEDHKLKSGTNTKKALQAVYSMMSWPDDVPPE
GWNRTRHVIILMTDGLHNMGGDPITVIDEIRDLLYIGKDRKNPREDYLDV
YVFGVGPLVNQVNINALASKKDNEQHVFKVKDMENLEDVFYQMIDESQSL
SLCGMVWEHRKGLDYHKQPWQAKISVIRPSKGHESCMGAVVSEYFVLTAA
HCFTVDDKEHSIKVSVGGEKRDLEIEVVLFHPNYNINGKKEAGIPEFYDY
DVALIKLKNKLKYGQTIRPICLPCTEGTTRALRLPPTTTCQQQKEELLPA
QDIKALFVSEEEKKLTRKEVYIKNGDKKGSCERDAQYAPGYDKVKDISEV
VTPRFLCTGGVSPYADPNTCRGDSGGPLIVHKRSRFIQVGVISWGVVDVC
KNQKRQKQVPAHARDFHINLFQVLPWLKEKLQDEDLGFL Factor Ba (SEQ ID NO: 17)
Signal peptide underlined
MGSNLSPQLCLMPFILGLLSGGVTTTPWSLARPQGSCSLEGVEIKGGSFR
LLQEGQALEYVCPSGFYPYPVQTRTCRSTGSWSTLKTQDQKTVRKAECRA
IHCPRPHDFENGEYWPRSPYYNVSDEISFHCYDGYTLRGSANRTCQVNGR
WSGQTAICDNGAGYCSNPGIPIGTRKVGSQYRLEDSVTYHCSRGLTLRGS
QRRTCQEGGSWSGTEPSCQDSFMYDTPQEVAEAFLSSLTETIEGVDAEDG
HGPGEQQKR In another embodiment, the disclosure provides an antibody that binds Factor Bb (SEQ ID NO:7), wherein said antibody comprises at least one HC CDR region having no more than two (2) amino acid additions, deletions or substitutions of any of SEQ ID NOs:1-3 or SEQ ID NOs:18-20, and/or at least one the LC CDR region having no more than two (2) amino acid additions, deletions or substitutions of any of SEQ ID NOs:4-6 or SEQ ID NOs:21-23. The various heavy chain and light chain variable regions of the disclosure are depicted in TABLE 3 and SEQ ID NOs:8-15 or SEQ ID NOs:24-31. In some embodiments, of particular use are antibodies with a HC CDR3 or LC CDR3 region. Additionally, in some embodiments antibodies can have one CDR having no more than two (2) amino acid additions, deletions or substitutions of the sequence selected from the HC CDR regions of any of SEQ ID NOs:1-3 or SEQ ID NOs:18-20 and a LC CDR having no more than two (2) amino acid additions, deletions, or substitutions of any of SEQ ID NOs:4-6 or SEQ ID NOs:21-23 (e.g., the antibody has two CDR regions, one HC CDR and one LC CDR, a specific embodiment are antibodies with both a HC CDR3 and a LC CDR3, for example, SEQ ID NOs:3 and 6).

TABLE 3

Light Chain Sequences

L1$_A$ (SEQ ID NO: 8)
DIQMTQSPSSLSASVGDRVTITCRASQNVNVWLSWYQQKPGKAPKLLIFK
ASNLQSGVPSRFSGSGSGTDFTLTISSLQPEDFATYYCQQGQSYPYTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

L2$_A$ (SEQ ID NO: 9)
DIQMTQSPSSLSASVGDTVTITCRASQNVNVWLSWYQQKPGKAPKLLIFK
ASNLQSGVPSRFSGSGSGTDFTLTISSLQPEDFATYYCQQGQSYPYTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

L3$_A$ (SEQ ID NO: 10)
DIQMTQSPSSLSASVGDTVTITCRASQNVNVWLSWYQQKPGKAPKLLIFK
AGNLQSGVPSRFSGSGSGTDFTLTISSLQPEDFATYYCQQGQSYPYTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

L4$_A$ (SEQ ID NO: 11)
DIQMTQSPSSLSASVGDTVTITCRASQSVNVWLSWYQQKPGKAPKLLIFK
AGNLQSGVPSRFSGSGSGTDFTLTISSLQPEDFATYYCQQGQSYPYTFGG
GTKLEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

L1$_B$ (SEQ ID NO: 24)
EIVLTQSPATLSLSPGERATLSCKASQSVDYDGDSYMNWYQQKPGQAPRL
LIYAASNLESGIPARFSGSGSGTDFTLTISSLEPEDFAVYYCQQSNADPY
TFGQGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC

L2$_B$ (SEQ ID NO: 25)
EIVLTQSPATLSLSPGERATLSCKASQSVDYDGDSYMNWYQQKPGQAPRL
LIYAASNLESGIPARFSGSGSGTDFTLTISSLEPEDGATYYCQQSNADPY
TFGQGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC

L3$_B$ (SEQ ID NO: 26)
EIVLTQSPATLSLSPGERATLGCKASQSVDYDGDSYMNWYQQKPGQAPRL
LIYAASNLESGIPARFSGSGSGTDFTLTISSLEPEDFAVYYCQQSNADPY
TFGQGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC

L4$_B$ (SEQ ID NO: 27)
EIVLTQSPATLSLSPGERATLGCKASQSVDYDGDSYMNWYQQKPGQAPRL
LIYAASNRESGIPARFSGSGSGTDFTLTISSLEPEDFAVYYCQQSNADPY
TFGQGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC

Heavy Chain Sequences

H1$_A$ (SEQ ID NO: 12)
QVQLVQSGAEVKKPGSSVKVSCKASGDIFSSHWIEWIRQAPGQGLEWMGE
ILPRSGITNYAQKFQGRVTFTADTSTSTAYMELSSLRSEDTAVYYCAINW
EDSWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVN
HKPSNTKVDKKVEPKSCDKTHL

H2$_A$ (SEQ ID NO: 13)
QVQLVQSGAEVKKPGSSVKVSCKASGDIFSSHWIEWIRQAPGQGLEWMGE
ILPRSGITHYAEKFQGRVTFTADTSTSTAYMELSSLRSEDTAVYYCAINW
EDSWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVN
HKPSNTKVDKKVEPKSCDKTHL

TABLE 3-continued

H3$_A$ (SEQ ID NO: 14)
QVQLVQSGAEVKKPGSSVKVSCKADGDIFSSHWIEWIRQAPGQGLEWMGE
ILPRSGITHYAEKFQGRVTFTADTSTSTAYMELSSLRSEDTAVYYCAINW
EDSWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVN
HKPSNTKVDKKVEPKSCDKTHL

H4$_A$ (SEQ ID NO: 15)
QVQLVQSGAEVKKPGSSVKVSCKADGDIFSSHWIEWVRQAPGQGLEWMGE
ILPRSGITNYAEKFQGRVTFTADTSTSTAYMELSSLRSEDTAVYYCAINW
EDSWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVN
HKPSNTKVDKKVEPKSCDKTHL

H1$_B$ (SEQ ID NO: 28)
EVQLVESGGGLVQPGGSLRLSCATSGFTFRDYYMSWVRQAPGKGLEWVGF
SRHRVYGYTTEYAASVKGRFTISRDNSKNTLYLQMNSLKTEDTAVYYCAR
DNPGYYAMDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHL

H2$_B$ (SEQ ID NO: 29)
EVQLVESGGGLVQPGGSLRLSCATSGFTFRDYYMSWVRQAPGKGLEWLGF
SRHRVYGYTPEYAASVKGRFTISRDNSKNTLYLQMNSLKTEDTAVYYCAR
DNPGYYAMDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHL

H3$_B$ (SEQ ID NO: 30)
EVQLVESGGGLVQPGGSLRLSCGTTGFTFRDYYMSWVRQAPGKGLEWLGF
SRHRVYGYTPEYAASVKGRFTISRDNSKNTLYLQMNSLKTEDTAVYYCAR
DNPGYYAMDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHL

H4$_B$ (SEQ ID NO: 31)
EVQLVESGGGLVQPGGSLRLSCGTTGFTFRDYYMSWVRQAPGKGLEWLGF
SRHRAYGYTPEYAASVKGRFTISRDNSKNTLYLQMNSLKTEDTAVYYCAR
DNPGYYAMDYWGQGTLVTVSSASTKGPSVFPLAPSSKSTSGGTAALGCLV
KDYFPEPVTVSWNSGALTSGVHTFPAVLQSSGLYSLSSVVTVPSSSLGTQ
TYICNVNHKPSNTKVDKKVEPKSCDKTHL

Variant CDR Sequences

An additional aspect of the disclosure provides for an isolated antibody that binds Factor Bb, wherein the isolated antibody comprises a heavy chain amino acid sequence having no more than two (2) amino acid additions, deletions or substitutions of any of SEQ ID NOs:12-15 or SEQ ID NOs:28-31, or a light chain amino acid sequence having no more than two (2) amino acid additions, deletions or substitutions of any of SEQ ID NOs:8-11 or SEQ ID NOs:24-27.

A further aspect of the disclosure provides for an isolated antibody that binds Factor Bb, wherein the isolated antibody comprises a heavy chain amino acid sequence having no more than two (2) amino acid additions, deletions or substitutions of any of SEQ ID NOs:12-15 or SEQ ID NOs: 28-31, and a light chain amino acid sequence having no more than two (2) amino acid additions, deletions or substitutions of any of SEQ ID NOs:8-11 or SEQ ID NOs:24-27. It is noted that any of the heavy chain sequences can be mixed and matched with any of the light chain sequences.

In another embodiment, the disclosure provides an antibody that binds a Factor Bb, wherein said antibody comprises at least one HC CDR region having no more than two (2) amino acid additions, deletions or substitutions of any HC CDR1, HC CDR2, or HC CDR3 region (as discussed above) of SEQ ID NOs:1-3 or SEQ ID NOs:18-20 and/or at least one LC CDR region having no more than two (2) amino acid additions, deletions or substitutions of any LC CDR1, LC CDR2, or LC CDR3 region (as discussed above) of SEQ ID NOs:4-6 or SEQ ID NOs:21-23. In this embodiment, of particular use are antibodies with a HC CDR3 or LC CDR3 region. Additional embodiments utilize antibodies with one CDR having no more than 2 amino acid additions, deletions or substitutions of the sequence selected from the HC CDR regions of any of SEQ ID NOs:1-3 or SEQ ID NOs:18-20 and a LC CDR region having no more than two (2) amino acid additions, deletions or substitutions of any of SEQ ID NOs:4-6 or SEQ ID NOs:21-23 (e.g., the antibody has two CDR regions, one HC CDR and one LC CDR, a specific embodiment are antibodies with both a HC CDR3 and a LC CDR3 region, for example SEQ ID NO:3 and 6).

As will be appreciated by those in the art, for any antibody with more than one CDR from the depicted sequences, any combination of CDRs independently selected from the depicted sequences is useful. Thus, antibodies with one, two, three, four, five or six of independently selected CDRs can be generated. However, as will be appreciated by those in the art, specific embodiments generally utilize combinations of CDRs that are non-repetitive, e.g., antibodies are generally not made with two HC CDR2 regions, etc.

An additional aspect of the disclosure provides for an isolated antibody that binds Factor Bb where the isolated antibody comprises a heavy chain amino acid sequence having no more than two (2) amino acid additions, deletions or substitutions of any of SEQ ID NOs:12-15 or SEQ ID NOs:28-31, or a light chain amino acid sequence having no more than two (2) amino acid additions, deletions or substitutions of any of SEQ ID NOs:8-11 or SEQ ID NOs:24-27.

A further aspect of the disclosure provides for an isolated antibody that binds Factor Bb where the isolated antibody comprises a heavy chain amino acid sequence having no more than two (2) amino acid additions, deletions or substitutions of any of SEQ ID NOs:12-15 or SEQ ID NOs:28-31, and a light chain amino acid sequence having no more than two (2) amino acid additions, deletions or substitutions of any of SEQ ID NOs:8-11 or SEQ ID NOs:24-27. It is noted that any of the heavy chain sequences can be mixed and matched with any of the light chain sequences.

Generally, the amino acid homology, similarity, or identity between individual variant CDRs, described herein, is at least 80% when compared to the sequences disclosed herein. In many cases the aa homology, similarity, or identity is at least 85%, 90%, 91%, 92%, 93%, 94%, 95%, 96%, 97%, 98%, and 99%.

Sequence Identity/Homology

As it is known in the art, a number of different programs can be used to identify the degree of sequence identity or similarity a protein or nucleic acid has to a known sequence. For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, *"Current Methods in Sequence Comparison and Analysis,"* Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values for proteins: overlap span=1, overlap fraction=0.125, word threshold, T=11. The HSP S and HSP S2 parameters are dynamic values and are established by the program itself depending upon the composition of the particular sequence and composition of the particular database against which the sequence of interest is being searched; however, the values can be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

Generally, the amino acid homology, similarity, or identity between individual variant CDRs or variable regions are at least 80% to the sequences depicted herein, and more typically with preferably increasing homologies or identities of at least 85%, 90%, 91%, 92%, 93%, 94%, 95%, 96%, 97%, 98%, 99%, and almost 100%.

In a similar manner, percent (%) nucleic acid sequence identity, with respect to the nucleic acid sequence of the disclosed antibodies, is the percentage of nucleotide residues in a candidate sequence that are identical with the nucleotide residues in the coding sequence of the antibody. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs and variant variable domain sequences are at least 80%, and more typically with preferably increasing homologies or identities of at least 85%, 85%, 90%, 91%, 92%, 93%, 94%, 95%, 96%, 97%, 98%, 99%, and almost 100%. In many cases non-identical nucleic acid sequences, because of the degeneracy of the genetic code, can code for the same amino acid sequence.

Homology between nucleotide sequences is often defined by their ability to hybridize to each other. In some embodiments, selective hybridization can refer to binding with high specificity. Polynucleotides, oligonucleotides and fragments thereof in accordance with the disclosure selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein.

The stringency of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

High stringency conditions are known in the art; see, for example Sambrook et al., 2001, supra, and *Short Protocols in Molecular Biology*, Second Edition, Ausubel et al. eds., John Wiley & Sons, 1992, both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, *Techniques In Biochemistry and Molecular Biology—Hybridization with Nucleic Acid Probes*, "Overview of principles of hybridization and the strategy of nucleic acid assays" (1993).

In some embodiments, stringent or high stringency conditions can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 C; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 .mu.g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

Generally, stringent conditions are selected to be about 5-10° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium Ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

In another embodiment, less stringent hybridization conditions are used; for example, moderate or low stringency conditions can be used, as are known in the art; see, Sambrook et al., 2001, supra; Ausubel et al., 1992, supra, and Tijssen, 1993, supra.

In some cases, moderately stringent conditions can include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In some embodiments, the disclosed antibodies and variants thereof can be prepared by site specific mutagenesis of nucleotides within a DNA sequence encoding the antibody. This can be achieved using cassette or PCR mutagenesis or other techniques well known in the art, to produce DNA encoding the variant, and thereafter expressing the recombinant DNA in cell culture as outlined herein. In some cases, antibody fragments comprising variant CDRs having up to about 100-150 residues can be prepared by in vitro synthesis using established techniques. These variant fragments can exhibit the same qualitative biological activity as the naturally occurring analogue, e.g., binding to Factor Bb and inhibiting complement, although variants can also be selected which have modified characteristics as will be more fully outlined below.

While the site or region for introducing an amino acid sequence variation is predetermined, the mutation per se need not be predetermined. For example, in order to optimize the a mutation at a given site, random mutagenesis can be conducted at the target codon or region and the expressed antibody CDR or variable region sequence variants screened for the optimal desired antibody activity. Techniques for making substitution mutations at predetermined sites in DNA having a known sequence are well known, for example, M13 primer mutagenesis and PCR mutagenesis. Screening of the mutants is done using assays of antibody activities, such as Factor Bb binding.

Amino acid substitutions are typically of single residues; insertions usually will be on the order of from about one (1) to about twenty (20) amino acid residues, although considerably larger insertions can be tolerated. Deletions range from about one (1) to about twenty (20) amino acid residues, although in some cases deletions can be much larger.

Substitutions, deletions, insertions or any combination thereof can be used to arrive at a final derivative or variant. Generally these changes are done on a few amino acids to minimize the alteration of the molecule, particularly the immunogenicity and specificity of the antibody. However, larger changes can be tolerated in certain circumstances. Conservative substitutions are generally made in accordance with the following chart depicted as Table 4.

TABLE 4

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Set |
| Trp | Tyr |
| Tyr | Trp, Phe |
| Val | Ile, Leu |

Changes in function or immunological identity can be made by selecting substitutions that are less conservative than those shown in Table 4. For example, substitutions can be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the disclosed Factor Bb antibody, as needed. Alternatively, variant can be selected wherein the biological activity of the disclosed antibody is altered. For example, glycosylation sites can be altered or removed as discussed herein.

Disclosed herein are polypeptide sequences homologous to SEQ ID NOs:1-6 and 8-15 and SEQ ID NOs:18-23 and SEQ ID NOs:24-31. Polypeptides disclosed herein can include amino acid sequences that are identical to the disclosed amino acid sequences. In other cases, the claimed polypeptides include amino acid sequences that can comprise conservative amino acid substitutions as compared to the disclosed sequence. Conservative amino acid substitutions can include amino acids that share characteristics with the substituted amino acid. In various cases, conservative substitution can be made without significant change in the structure or function of the polypeptide.

Conservative amino acid substitutions can be made on the basis of relative similarity of side-chain, size, charge, hydrophobicity, hydrophilicity, isoelectric point, etc. In various cases, substitutions can be assayed for their effect on the function of the protein by routine testing. Conserved amino acid substitutions include amino acids with similar hydrophilicity value, as wherein amino acids have a hydropathic index which can be based upon an amino acid's hydrophobicity and charge. In various cases, conserved amino acid substitutions can be made between amino acids of the same class, for example non-polar amino acids, acidic amino acids, basic amino acids, and neutral amino acids. Conservative substitutions can also be based upon size or volume. Amino acids can also be classified based upon their ability to form or break a given structure, such as an alpha helix, beta sheet, or intra- or inter-molecular interaction. In various cases conservative amino acid substitutions are based upon more than one characteristic.

Currently disclosed polypeptides can include both natural and non-natural amino acids. In various cases, natural amino acid side chains can be substituted with non-natural side chains. In various cases, amino acids can be derivatized.

The disclosed polypeptides include polypeptides that are homologous to the sequences of SEQ ID NO:1-6 and 8-15 and SEQ ID NO:18-31. Homology can be expressed as % identity or % similarity or % positive. In various cases, % identity is a percentage of amino acids that are identical between two aligned polypeptides, and % similar or % positive is a percentage of amino acids that are non-identical but represent conservative substitutions. A conservative substitution may be a substitution of a like-charged amino acid, a like-sized amino acid, a like-polarity amino acid, etc. For example, lysine to arginine can be considered a conservative substitution where charge is considered.

In various cases, two polypeptides can be aligned by algorithms, for example BLASTp. In various cases, the BLASTp parameters can be set with a maximum target sequence length equal to, greater, or less than the length of the longer of the two polypeptides, the expect threshold can be set to 10, the word size to 3, and scoring matrix can be BLOSUM62, with gap costs of 11 for existence and 1 for extension. BLASTp can report homology of aligned polypeptides as "Identities" and "Positives." The aligned sequences can include gaps to achieve the alignment.

In various cases, homology of amino acid sequences can reflect the percentage of identity or positives when optimally aligned as described above. In various cases, the % homology (% positive) or % identity can be calculated by dividing the number of aligned amino acids within a comparison window. A comparison window can be the entire length of one or the other polypeptides, if the two polypeptides are of unequal length. In other cases, the comparison window can be a portion of one of the polypeptides. In various cases the comparison window for measuring homology or identity of two polypeptide sequences is greater than about 40 aa (amino acids), 45 aa, 50 aa, 55 aa, 60 aa, 65 aa, 70 aa, 75 aa, 80 aa, 85 aa, 90 aa, 95 aa, 100 aa, 150 aa, or 200 aa, and/or less than about 200 aa, 150 aa, 100 aa, 95 aa, 90 aa, 85 aa, 80 aa, 75 aa, 70 aa, 65 aa, 60 aa, 55 aa, 50 aa, or 45 aa. In some embodiment, as in the case with CDR sequences, the comparison window may be less than 40 aa, for example between less than about 25 aa, 24 aa, 23 aa, 22 aa, 21 aa, 20 aa, 19 aa, 18 aa, 17 aa, 16 aa, 15 aa, 14 aa, 13 aa, 12 aa, 11 aa, 10 aa, 9 aa, 8 aa, 7 aa, 6 aa, 5 aa, or 4 aa, and greater than about 3 aa, 4 aa, 5 aa, 6 aa, 7 aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, or 24 aa.

In various cases, the claimed amino acid sequences can have % identity or % homology (% positive) over a given comparison window, that is greater than about 60%, 65%, 70%, 75%, 80%, 85%, 90%, 91%, 92%, 93%, 94%, 95%, 96%, 97%, 98%, or 99% and/or less than about 100%, 99%, 98%, 97%, 96%, 95%, 94%, 93%, 92%, 91%, 90%, 85%, 80%, 75%, or 70%.

In various cases, a sequence alignment can be performed using various algorithms, including dynamic, local, and global alignment. For example, the algorithm of Smith and Waterman, 1981, Adv. Appl. Math 2: 482; the alignment algorithm of Needleman and Wunsch, 1970, J. Mol. Biol. 48:443; the similarity method of Pearson and Lipman, 1988, Proc. Natl. Acad. Sci. USA 85: 2444. In various cases, computer programs can implement these algorithms (such as EMBOSS, GAP, BESTFIT, FASTA, TFASTA BLAST, BLOSUM, etc.).

In alternative cases, conserved amino acid substitutions can be made where an amino acid residue is substituted for another in the same class, for example where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

In some cases, conserved amino acid substitutions can be made where an amino acid residue is substituted for another having a similar hydrophilicity value (e.g., within a value of plus or minus 2.0), where the following can be an amino acid having a hydropathic index of about −1.6 such as Tyr (−1.3) or Pro (−1.6)s are assigned to amino acid residues: Arg (+3;0); Lys (+3.0); Asp (+3.0); Glu (+3.0); Ser (+0.3); Asn (+0.2); Gin (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative cases, conserved amino acid substitutions can be made where an amino acid residue is substituted for another having a similar hydropathic index (e.g., within a value of plus or minus 2.0). In such cases, each amino acid residue can be assigned a hydropathic index on the basis of its hydrophobicity and charge characteristics, as follows: lie (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative cases, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (J. Mol. Bio. 179:125-142, 184). Genetically encoded hydrophobic amino acids include Gly, Ala, Phe, Val, Leu, lie, Pro, Met and Trp, and genetically encoded hydrophilic amino acids include Thr, His, Glu, Gln, Asp, Arg, Ser, and Lys. Non-genetically encoded hydrophobic amino acids include t-butylalanine, while non-genetically encoded hydrophilic amino acids include citrulline and homocysteine.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which can contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR, etc., where R is independently (C$_1$-C$_6$) alkyl, substituted (C$_1$-C$_6$) alkyl, (C$_0$-C$_6$) alkenyl, substituted (C$_1$-C$_6$) alkenyl, (C$_1$-C$_6$) alkynyl, substituted (C$_0$-C$_6$) alkynyl, (C$_5$-C$_{20}$) aryl, substituted (C$_0$-C$_{20}$) aryl, (C$_6$-C$_{26}$) alkaryl, substituted (C$_6$-C$_{26}$) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe, Tyr, and Trp.

An non-polar or apolar amino acid is a hydrophobic amino acid with a side chain that is uncharged at physiological pH and which has bonds in which a pair of electrons shared in common by two atoms is generally held equally by each of the two atoms (i.e., the side chain is not polar). Genetically encoded apolar amino acids include Gly, Leu, Val, Ile, Ala, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

A % amino acid sequence identity value is determined by the number of matching identical residues divided by the total number of residues of the "longer" sequence in the comparison window. The "longer" sequence is the one having the most actual residues in the comparison window (gaps introduced by WU-Blast-2 to maximize the alignment score are ignored).

The alignment can include the introduction of gaps in the sequences to be aligned. In addition, for sequences which contain either more or fewer amino acids than the protein encoded by the sequence the disclosed polypeptide, it is understood that in one case, the percentage of sequence identity will be determined based on the number of identical amino acids in relation to the total number of amino acids. In percent identity calculations relative weight is not assigned to various manifestations of sequence variation, such as, insertions, deletions, substitutions, etc.

In one case, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Scaffolds

As noted herein, the antibodies of the present disclosure can comprise a scaffold structure into which the CDR(s) described above can be grafted. In one embodiment, the scaffold structure is a traditional antibody structure, that is, an antibody comprising two heavy and two light chain variable domain sequences. In some cases, the antibody combinations described herein can include additional components (framework, J and D regions, constant regions, etc.)

that make up a heavy and/or a light chain. Some embodiments include the use of human scaffold components.

Accordingly, in various embodiments, the antibodies of the disclosure comprise the scaffolds of traditional antibodies. In some embodiments, the disclosed antibodies can be human and monoclonal antibodies, bispecific antibodies, diabodies, minibodies, domain antibodies, synthetic antibodies, chimeric antibodies, antibody fusions, and fragments of each, respectively. The above described CDRs and combinations of CDRs can be grafted into any of the following scaffolds.

Chimeric antibodies of the present disclosure can comprise a heavy and/or light chain sequence that is identical or homologous to the corresponding sequences derived from a particular species. For example, in one embodiment the anti-Factor Bb antibody is a chimeric antibody comprising a human Fc domain, while the remainder of the antibody can be identical or homologous to corresponding mouse or rodent sequences. Chimeric antibodies can be fragments of such antibodies, so long as the fragments exhibit the desired biological activity and comprise sequence that is derived from another species, class of antibody, or subclass of antibody (U.S. Pat. No. 4,816,567; and Morrison et al. (1984) Proc. Natl. Acad. Sci. USA 81:6851-6855).

In some embodiments, a variable region of the presently disclosed anti-Factor Bb antibody comprises at least three heavy or light chain CDRs, see, supra (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), embedded within a framework region (designated framework regions 1-4, FR1, FR2, FR3, and FR4, by Kabat et al., 1991, supra; see also Chothia and Lesk, 1987, supra).

In some cases, the antibody can be comprised of a heavy chain variable domain sequence or a light chain variable domain sequence. In some cases the heavy or light chain variable domain sequence may comprise a sequence selected from the sequences of Table 3.

Traditional antibody structural units, in most cases, comprise a tetramer. Each tetramer is typically composed of two identical pairs of polypeptide chains, each pair having one light chain (typically having a molecular weight of about 25 kDa) and one heavy chain (typically having a molecular weight of about 50-70 kDa). The amino-terminal portion of each chain includes a variable region of about 100 to 110 or more amino acids primarily responsible for antigen recognition. The carboxy-terminal portion of each chain defines a constant region, while the heavy chain may comprise a total of three constant regions (CH1, CH2, and CH3), wherein the constant regions may aid in regulating effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to IgG1, IgG2, IgG3, and IgG4. IgM has subclasses, including, but not limited to, IgM1 and IgM2.

Within light and heavy chains, the variable and constant regions are joined by a "J" region of about twelve (12) or more amino acids, with the heavy chain also including a "D" region of about ten (10) more amino acids. See, generally, Paul, W., ed., 1989, Fundamental Immunology Ch. 7, 2nd ed. Raven Press, N.Y. The variable regions of each light and heavy chain pair form the antibody binding site.

Some naturally occurring antibodies, for example found in camels and llamas, are dimers consisting of two heavy chains and include no light chains. Muldermans et al., 2001, *J. Biotechnol.* 74:277-302; Desmyter et al., 2001, *J. Biol. Chem.* 276:26285-26290. Crystallographic studies of a camel antibody have revealed that the CDR3 regions form a surface that interacts with the antigen and thus is critical for antigen binding like in the more typical tetrameric antibodies. The disclosure encompasses dimeric antibodies consisting of two heavy chains, or fragments thereof, that can bind to and/or inhibit the biological activity of Factor Bb.

The variable regions of the heavy and light chains typically exhibit the same general structure of relatively conserved framework regions (FR) joined by three complementarity determining regions or CDRs. The CDRs comprise hypervariable regions of an antibody that are responsible for antigen recognition and binding. The CDRs from the two chains of each pair are aligned and supported by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest. Chothia et al., 1987, *J. Mol. Biol.* 196:901-917; Chothia et al., 1989, *Nature* 342: 878-883.

CDRs constitute the major surface contact points for antigen binding. See, e.g., Chothia and Lesk, 1987, *J. Mol. Biol.* 196:901-917. Further, CDR3 of the light chain and, especially, CDR3 of the heavy chain may constitute the most important determinants in antigen binding within the light and heavy chain variable regions. See, e.g., Chothia and Lesk, 1987, supra; Desiderio et al., 2001, *J. Mol. Biol.* 310:603-615; Xu and Davis, 2000, Immunity 13:37-45; Desmyter et al., 2001, *J. Biol. Chem.* 276:26285-26290; and Muyldermans, 2001, *J. Biotechnol.* 74:277-302. In some antibodies, the heavy chain CDR3 appears to constitute the major area of contact between the antigen and the antibody. Desmyter et al., 2001, supra. In vitro selection schemes in which CDR3 alone is varied can be used to vary the binding properties of an antibody. Muyldermans, 2001, supra; Desiderio et al., 2001, supra.

Naturally occurring antibodies typically include a signal sequence, which directs the antibody into the cellular pathway for protein secretion and which is not present in the mature antibody. A polynucleotide encoding an antibody of the disclosure may encode a naturally occurring signal sequence or a heterologous signal sequence as described below.

In one embodiment, the anti-Factor Bb antibody is a monoclonal antibody, with from one (1) to six (6) of the CDRs, as outlined herein. The antibodies of the disclosure can be of any type including IgM, IgG (including IgG1, IgG2, IgG3, IgG4), IgD, IgA, or IgE antibody. In specific embodiment, the antibody is an IgG type antibody. In an even more specific embodiment, the antibody is an IgG2 type antibody.

In some embodiments, the antibody can comprise complete heavy and light chains, the CDRs are all from the same species, e.g., human. Alternatively, for example in embodiments wherein the antibody contains less than six CDRs from the sequences outlined above, additional CDRs can be either from other species (e.g., murine CDRs), or can be different human CDRs than those depicted in the sequences. For example, human HC CDR3 and LC CDR3 regions from the appropriate sequences identified herein can be used, with HC CDR1, HC CDR2, LC CDR1 and LC CDR2 being optionally selected from alternate species, or different human antibody sequences, or combinations thereof. For example, the CDRs of the disclosure can replace the CDR regions of commercially relevant chimeric or humanized antibodies.

Specific embodiments utilize scaffold components of the antibodies that are human components.

In some embodiments, however, the scaffold components can be a mixture from different species. As such, the antibody can be a chimeric antibody and/or a humanized antibody. In general, both chimeric antibodies and humanized antibodies can be antibodies that combine regions or amino acids from more than one species. For example, chimeric antibodies, in most embodiments, comprise variable region(s) from a mouse, rat, rabbit, or other suitable non-human animal, and the constant region(s) from a human.

Humanized antibodies are antibodies that are originally derived from non-human antibodies, for example a mouse antibody. In various embodiments of a humanized anti-Factor Bb antibody, the variable-domain framework regions or framework amino acids, which are derived from a non-human antibody, can be changed to be amino acid identities found at corresponding positions in human antibodies. In some embodiments of a humanized antibody, the entire antibody, except the CDRs, can be encoded by a polynucleotide of human origin or is identical to such an antibody except within its CDRs. In other embodiments, a humanized antibody may comprise specific amino acid positions whose identity has been changed to the identity of the same or similar position in a corresponding human antibody. The CDRs, some or all of which can be encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, *Nature* 321: 522-525, Verhoeyen et al., 1988, *Science* 239:1534-1536. Humanized antibodies can also be generated using mice with a genetically engineered immune system. Roque et al., 2004, *Biotechnol. Prog.* 20:639-654. In some embodiments, the CDRs can be human, and thus both humanized and chimeric antibodies in this context include some non-human CDRs. In some cases, humanized antibodies can be generated that comprise the HC CDR3 and LC CDR3 regions, with one or more of the other CDR regions being of a different special origin.

In one embodiment, the Factor Bb antibody can be a multispecific antibody, and notably a bispecific antibody, (e.g. diabodies). These are antibodies that bind to two (or more) different antigens, for example Factor Bb, and another antigen, or two different epitopes of Factor Bb. Diabodies can be manufactured in a variety of ways known in the art (Holliger and Winter, 1993, *Current Opinion Biotechnol.* 4:446-449), e.g., prepared chemically or from hybrid hybridomas.

In one embodiment, the Factor Bb antibody is a minibody. Minibodies are minimized antibody-like proteins comprising a scFv joined to a CH3 domain. Hu et al., 1996, *Cancer Res.* 56:3055-3061.

In one embodiment, the Factor Bb antibody is a domain antibody; see, for example U.S. Pat. No. 6,248,516. Domain antibodies (dAbs) are functional binding domains of antibodies, corresponding to the variable regions of either the heavy (VH) or light (VL) chains of human antibodies dABs have a molecular weight of approximately 13 kDa, or less than one-tenth the size of a full antibody. dABs are well expressed in a variety of hosts including bacterial, yeast, and mammalian cell systems. In addition, dAbs are highly stable and retain activity even after being subjected to harsh conditions, such as freeze-drying or heat denaturation. See, for example, U.S. Pat. Nos. 6,291,158; 6,582,915; 6,593,081; 6,172,197; US Serial No. 2004/0110941; European Patent 0368684; U.S. Pat. No. 6,696,245, WO04/058821, WO04/003019 and WO03/002609, all incorporated entirely by reference.

In one embodiment, the Factor Bb antibody is an antibody fragment, that is a fragment of any of the antibodies outlined herein that retain binding specificity to Factor Bb. In various embodiments, the antibodies are a F(ab), F(ab'), F(ab')2, Fv, or a single chain Fv fragments. At a minimum, an antibody, as meant herein, comprises a polypeptide that can bind specifically to an antigen, wherein the polypeptide comprises all or part of a light and/or a heavy chain variable region.

Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, *Nature* 341:544-546) which consists of a single variable, (v) isolated CDR regions, (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, *Science* 242:423-426, Huston et al., 1988, *Proc. Natl. Acad. Sci. U.S.A.* 85:5879-5883), (viii) bispecific single chain Fv dimers (PCT/US92/09965) and (ix) diabodies or triabodies, multivalent or multispecific fragments constructed by gene fusion (Tomlinson et. al., 2000, *Methods Enzymol.* 326:461-479; WO94/13804; Holliger et al., 1993, *Proc. Natl. Acad. Sci. U.S.A.* 90:6444-6448). The antibody fragments can be modified. For example, the molecules can be stabilized by the incorporation of disulphide bridges linking the VH and VL domains (Reiter et al., 1996, *Nature Biotech.* 14:1239-1245). Again, as outlined herein, the non-CDR components of these fragments are preferably human sequences.

In one embodiment, the Factor Bb antibody is a traditional antibody, for example a human immunoglobulin. In this embodiment, as outlined above, specific structures comprise complete heavy and light chains depicted comprising the CDR regions. Additional embodiments utilize one or more of the CDRs of the disclosure, with the other CDRs, framework regions, J and D regions, constant regions, etc., coming from other human antibodies. For example, the CDRs of the disclosure can replace the CDRs of any number of human antibodies, particularly commercially relevant antibodies.

In one embodiment, the Factor Bb antibody is an antibody fusion protein (e.g. an antibody conjugate). In this embodiment, the antibody is fused to a conjugation partner. The conjugate partner can be proteinaceous or non-proteinaceous; the latter generally being generated using functional groups on the antibody (see the discussion on covalent modifications of the antibodies) and on the conjugate partner. For example linkers are known in the art; for example, homo- or hetero-bifunctional linkers as are well known (see, Pierce Chemical Company catalog, technical section on cross-linkers, pages 155-200, incorporated herein by reference).

In one embodiment, the Factor Bb antibody is an antibody analog. In some cases antibody analogs can be referred to as synthetic antibodies. For example, a variety of recent work utilizes either alternative protein scaffolds or artificial scaffolds with grafted CDRs. Such scaffolds include, but are not limited to, mutations introduced to stabilize the three-dimensional structure of the antibody as well as wholly synthetic scaffolds consisting for example of biocompatible polymers. See, for example, Korndorfer et al., 2003, *Proteins: Structure, Function, and Bioinformatics*, Volume 53, Issue 1:121-129. Roque et al., 2004, *Biotechnol. Prog.* 20:639-654. In addition, peptide antibody mimetics (PAMs) can be used, as well as work based on antibody mimetics utilizing fibronectin components as a scaffold.

VH and VL Variants

As outlined above, in some embodiments the disclosure provides antibodies comprising, or consisting of a heavy chain variable region comprising SEQ ID NO:1-3 and/or a light chain variable region of SEQ ID NO:4-6, respectively, or fragments thereof as defined above. Thus, in those embodiments, the antibody comprises not only at least one CDR or variant, but also at least part of a depicted framework sequence. In addition, the disclosure encompasses variants of such heavy chain variable sequences or light chain variable sequences.

A variant variable region, generally shares an amino acid homology, similarity, or identity of at least 80% with those a parent variable region, such as those disclosed herein. In some embodiments, the variant and parent sequence homologies or identities are at least 75%, 80%, 85%, 90%, 91%, 92%, 93%, 94%, 95%, 96%, 97%, 98%, 99% and almost 100%. The nucleic acid sequence homology, similarity, or identity between the nucleotide sequences encoding individual variant VHs and VLs and the nucleic acid sequences depicted herein are at least 70% with those depicted herein, and more typically with preferably increasing homologies or identities of at least 80%, 85%, 90%, 91%, 92%, 93%, 94%, 95%, 96%, 97%, 98%, 99% and almost 100%. In addition, a variant variable region can, in many embodiments, shares the biological function, including, but not limited to, at least 90%, 91%, 92%, 93%, 94%, 95%, 96%, 97%, 98% or 99% of the specificity and/or activity of the parent CDR. In some case, homology and/or identity is only measured outside the CDR sequences, which can be identical. In other cases, the homology and/or identity is measured throughout the entire sequence, including CDR sequences. In some embodiments, constant region variants may also be included.

In various cases, homology of amino acid sequences can reflect the percentage of identity or positives when optimally aligned as described above. In various cases, the % homology (% positive) or % identity can be calculated by dividing the number of aligned amino acids within a comparison window. A comparison window can be the entire length of one or the other polypeptides, if the two polypeptides are of unequal length. In other cases, the comparison window can be a portion of one of the polypeptides. In various cases the comparison window for measuring homology or identity of two polypeptide sequences is greater than about 40 aa (amino acids), 45 aa, 50 aa, 55 aa, 60 aa, 65 aa, 70 aa, 75 aa, 80 aa, 85 aa, 90 aa, 95 aa, 100 aa, 150 aa, or 200 aa, and/or less than about 200 aa, 150 aa, 100 aa, 95 aa, 90 aa, 85 aa, 80 aa, 75 aa, 70 aa, 65 aa, 60 aa, 55 aa, 50 aa, or 45 aa. In some embodiment, as in the case with CDR sequences, the comparison window may be less than 40 aa, for example between less than about 25 aa, 24 aa, 23 aa, 22 aa, 21 aa, 20 aa, 19 aa, 18 aa, 17 aa, 16 aa, 15 aa, 14 aa, 13 aa, 12 aa, 11 aa, 10 aa, 9 aa, 8 aa, 7 aa, 6 aa, 5 aa, or 4 aa, and greater than about 3 aa, 4 aa, 5 aa, 6 aa, 7 aa, 8 aa, 9 aa, 10 aa, 11 aa, 12 aa, 13 aa, 14 aa, 15 aa, 16 aa, 17 aa, 18 aa, 19 aa, 20 aa, 21 aa, 22 aa, 23 aa, or 24 aa.

In various cases, the claimed amino acid sequences can have % identity or % homology (% positive) over a given comparison window, that is greater than about 70%, 75%, 80%, 85%, 90%, 91%, 92%, 93%, 94%, 95%, 96%, 97%, 98%, or 99% and/or less than about 100%, 99%, 98%, 97%, 96%, 95%, 94%, 93%, 92%, 91%, 90%, 85%, 80%, or 75%.

Covalent Modifications of Anti-Factor Bb Antibodies

Covalent modifications of antibodies are included within the scope of this disclosure, and are generally, but not always, done post-translationally. For example, several types of covalent modifications of the antibody are introduced into the molecule by reacting specific amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues can be made, with particular interest in introducing spectral labels into tyrosyl residues by reaction with aromatic diazonium compounds or tetranitromethane. Most commonly, N-acetylimidizole and tetranitromethane are used to form 0-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking antibodies to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this disclosure.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Glycosylation

Another type of covalent modification of the antibodies included within the scope of this disclosure comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbohydrate moiety to the side chain of an asparagine residue. The tri-peptide sequences asparagine-X-serine and asparagine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the disclosed antibody is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the antibody's amino acid sequence is preferably altered through changes at the DNA level, particularly by mutating the DNA encoding the target polypeptide at preselected bases such that codons are generated that will translate into the desired amino acids.

Another means of increasing the number of carbohydrate moieties on the antibody is by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) can be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem., pp.* 259-306.

Removal of carbohydrate moieties present on the starting antibody can be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites can be prevented by the use of the compound tunicamycin as described by Duskin et al., 1982, *J. Biol. Chem.* 257:3105. Tunicamycin blocks the formation of protein-N-glycoside linkages.

PEGylation

Another type of covalent modification of the antibody comprises linking the antibody to various nonproteinaceous polymers, including, but not limited to, various polyols such as polyethylene glycol, polypropylene glycol or polyoxy-alkylenes, in the manner set forth in U.S. Pat. Nos. 4,640,835; 4,496,689; 4,301,144; 4,670,417; 4,791,192 and/or 4,179,337, all incorporated entirely by reference. In addition, as is known in the art, amino acid substitutions can be made in various positions within the antibody to facilitate the addition of polymers such as PEG.

Labels

In some embodiments, the covalent modification of the antibodies of the disclosure comprises the addition of one or more labels.

The term "labelling group" means any detectable label. Examples of suitable labelling groups include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antibody via spacer arms of various lengths to reduce potential steric hindrance. Various methods for labelling proteins are known in the art and can be used in performing the present disclosure.

In general, labels fall into a variety of classes, depending on the assay in which they are to be detected: a) isotopic labels, which can be radioactive or heavy isotopes; b) magnetic labels (e.g., magnetic particles); c) redox active moieties; d) optical dyes; enzymatic groups (e.g. horseradish peroxidase, β-galactosidase, luciferase, alkaline phosphatase); e) biotinylated groups; and f) predetermined polypeptide epitopes recognized by a secondary reporter (e.g., leucine zipper pair sequences, binding sites for secondary antibodies, metal binding domains, epitope tags, etc.). In some embodiments, the labelling group is coupled to the antibody via spacer arms of various lengths to reduce potential steric hindrance. Various methods for labelling proteins are known in the art and can be used in performing the present disclosure.

Specific labels include optical dyes, including, but not limited to, chromophores, phosphors and fluorophores, with the latter being specific in many instances. Fluorophores can be either "small molecule" fluores, or proteinaceous fluores.

A fluorescent label can be any molecule that can be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor™ 350, Alexa Fluor™ 430, Alexa Fluor™ 488, Alexa Fluor™ 546, Alexa Fluor™ 568, Alexa Fluor™ 594, Alexa Fluor™ 633, Alexa Fluor™ 660, Alexa Fluor™ 680), Cascade Blue, Cascade Yellow and R-phycoerythrin (PE) (Molecular Probes™, Eugene, Oreg.), FITC, Rhodamine, and Texas Red (Pierce, Rockford, Ill.), Cy5, Cy5.5, Cy7 (Amersham Life Science, Pittsburgh, Pa.). Suitable optical dyes, including fluorophores, are described in Molecular Probes Handbook by Richard P. Haugland, hereby expressly incorporated by reference.

Suitable proteinaceous fluorescent labels also include, but are not limited to, green fluorescent protein, including a *Renilla, Ptilosarcus,* or *Aequorea* species of GFP (Chalfie et al., 1994, *Science* 263:802-805), EGFP (Clontech Laboratories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, *Biotechniques* 24:462-471; Heim et al., 1996, *Curr. Biol.* 6:178-182), enhanced yellow fluorescent protein (EYFP, Clontech Laboratories, Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and *Renilla* (WO92/15673, WO95/07463, WO98/14605, WO98/26277, WO99/49019, U.S. Pat. Nos. 5,292,658, 5,418,155, 5,683,888, 5,741,668, 5,777,079, 5,804,387, 5,874,304, 5,876,995, 5,925,558), all incorporated entirely by reference.

Polynucleotides Encoding Anti-Factor Bb Antibodies

In certain aspects, the disclosure provides nucleic acid molecules encoding the antibodies described herein. In some cases the disclosed nucleic acids code for IgGs, variable regions, or CDRs described herein. Nucleic acids include both DNA and RNA molecules. Nucleic acids can be either natural or synthetic nucleic acids. Nucleic acids of the present disclosure are typically polynucleic acids; that is, polymers of individual nucleotides that are covalently joined by 3', 5' phosphodiester bonds. In various cases the nucleotide sequences can be single-stranded, double stranded, or a combination thereof. In some variations, the nucleotide sequences can comprise natural nucleic acids, synthetic nucleic acids, non-natural nucleic acids, and/or nucleic acid analogs. The nucleotide sequences can further comprise other non-nucleic acid molecules such as amino acids, and other monomers.

In many embodiments, the coding sequence may be an isolated nucleic acid molecule. The isolated nucleic acid molecule is identified and separated from at least one component with which it is ordinarily associated in the natural source. In some cases a component can be a nucleotide sequence, protein, or non-proteinaceous molecule. An isolated anti-Factor Bb antibody-encoding nucleic acid molecule is other than in the form or setting in which it is found in nature. Isolated anti-Factor Bb antibody-encoding nucleic acid molecules therefore are distinguished from the encoding nucleic acid molecule(s) as they exist in natural cells. However, an isolated anti-Factor Bb antibody-encoding nucleic acid molecule includes anti-Factor Bb antibody-encoding nucleic acid molecules contained in cells that ordinarily express anti-Factor Bb antibody where, for example, the nucleic acid molecule is in a chromosomal location different from that of natural cells. Isolated nucleic acid molecules therefore are distinguished from the nucleic acid molecule as it exists in an organism. However, in some cases an isolated nucleic acid molecule can be a nucleic acid contained within a cell, for example, wherein the isolated nucleic acid molecule is introduced into a cell and resides in either an extrachromosomal location or in a chromosomal location different from its native location.

Depending on its use, the nucleic acid can be double stranded, single stranded, or contain portions of both double stranded or single stranded sequence. As will be appreciated by those in the art, the depiction of a single strand ("Watson") also defines the sequence of the other strand ("Crick"). A recombinant nucleic can be a nucleic acid, originally formed in vitro, in general, by the manipulation of nucleic acid by endonucleases, in a form not normally found in nature. Thus an isolated antibody can be encoded by a nucleic acid, in a linear form, or an expression vector formed in vitro by ligating DNA molecules that are not normally joined, are both considered recombinant for the purposes of this disclosure. It is understood that once a recombinant nucleic acid, with all necessary control elements, is made and reintroduced into a host cell or organism, it can replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the disclosure.

In some embodiments, the recombinant nucleic acid may comprise one or more control elements or control sequences. Control element and control sequence refers to nucleic acid sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers. As used herein, an operably linked sequence, is a nucleic acid sequence in a functional relationship with another nucleic acid sequence. For example, nucleic acid coding sequences can be operably linked to nucleic acid control sequences. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. In most embodiments, an operably linked sequence is a DNA sequence covalently linked to, for example, a secretory leader sequence. In many embodiments, enhancer sequences are not required to be adjacent to a coding sequence, rather the two sequences may be separated by one or more nucleic acids.

In various cases, the nucleic acids of the disclosed nucleotide sequences can include nucleotides that are metabolized in a manner similar to naturally occurring nucleotides. Also included are nucleic-acid-like structures with synthetic backbone analogues including, without limitation, phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs) (see, e.g.: "Oligonucleotides and Analogues, a Practical Approach," edited by F. Eckstein, IRL Press at Oxford University Press (1991); "Antisense Strategies," Annals of the New York Academy of Sciences, Volume 600, Eds. Baserga and Denhardt (NYAS 1992); Milligan (1993) J. Med. Chem. 36:1923-1937; and "Antisense Research and Applications" (1993, CRC Press)). PNAs contain non-ionic backbones, such as N-(2-aminoethyl) glycine units. Phosphorothioate linkages are described in: WO 97/03211; WO 96/39154; and Mata (1997) Toxicol. Appl. Pharmacol. 144: 189-197. Other synthetic backbones encompassed by this term include methyl-phosphonate linkages or alternating methyl-phosphonate and phosphodiester linkages (Strauss-Soukup (1997) Biochemistry 36: 8692-8698), and benzyl-phosphonate linkages (Samstag (1996) Antisense Nucleic Acid Drug Dev 6: 153-156).

As will be appreciated by those in the art, due to the degeneracy of the genetic code, an extremely large number of nucleic acids can be made, all of which encode the CDRs (and heavy and light chains or other components of the antibody) of the present disclosure. Thus, having identified a particular amino acid sequence, those skilled in the art could make any number of different nucleic acids, by simply modifying the sequence of one or more codons in a way which does not change the amino acid sequence of the encoded protein.

In various cases, nucleotide sequences encoding the polypeptide sequences of SEQ ID NO:1-6 and 8-15 and 18-31 are included. These nucleotide coding sequences can be translated into a polypeptide having an amino acid sequence identical to the disclosed polypeptide sequence. In many cases, nucleotides coding for identical polypeptides, may not have identical nucleotide sequences. This is due to the degeneracy of the genetic code. The disclosed coding sequences can further comprise untranslated sequences, for example polyadenylation sequences. The inventive coding sequences can also comprise intron or intervening, non-translated, sequence that are spliced out of a transcribed mRNA prior to translation. In various cases the transcribed mRNA can be capped with a terminal 7-methylguanosine. In some embodiments, the coding sequences will include coding sequences for amino acids that do not appear in the final antibody, for example sequences required for export of the antibody.

In some variations, due to the degeneracy of the genetic code, multiple nucleotide coding sequences can encode the same polypeptide sequence. These inventive nucleic acid coding sequences can also be homologous to nucleotide sequences that encode the disclosed polypeptides. The nucleotide coding sequences can be aligned by BLASTn, as described above. In various cases the homology (or identities in BLASTn) of these aligned nucleotide sequences can be greater than about 40%, 45%, 50%, 55%, 60%, 65%, 70%, 75%, 80%, 85%, 90%, or 95% and/or less than about 100%, 95%, 90%, 85%, 80%, 75%, 70%, 65%, 60%, 55%, 50%, or 45%. In various cases, the homologous aligned sequences can be less than about 700 nt, 600 nt, 500 nt, 400 nt, 300 nt, 200 nt, 100 nt, 90 nt, 80 nt, 70 nt, 60 nt, 50 nt or 40 nt, and/or more than about 50 nt, 60 nt, 70 nt, 80 nt, 90 nt, 100 nt, 200 nt, 300 nt, 400 nt, 500 nt, or 600 nt.

In various cases, the coding sequence directs transcription of a ribonucleic acid sequence that can be translated into amino acid sequence according to the standard genetic code. In various cases, the code can include variations to the canonical code. In some variations, the coding sequence can include introns, or intervening sequences that do not code for amino acids, but can be transcribed and later removed before the ribonucleic acid is translated into a polypeptide.

Methods of Producing Antibodies

The present disclosure also provides expression systems and constructs in the form of plasmids, expression vectors, transcription or expression cassettes which comprise at least one polynucleotide as above. In addition, the disclosure provides host cells comprising such expression systems or constructs.

Typically, expression vectors used in any of the host cells will contain sequences for plasmid maintenance and for cloning and expression of exogenous nucleotide sequences. Such sequences, collectively referred to as flanking sequences in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the Factor Bb antibody coding sequence; the oligonucleotide sequence can encode a polyHis tag (such as hexaHis), or another "tag" such as FLAG, HA (hemagglutinin influenza virus), or myc, for which commercially available antibodies exist. This tag is typically fused to the polypeptide upon expression of the polypeptide, and can serve as a means for affinity purification or detection of the Factor Bb antibody from the host cell. Affinity purification can be accomplished, for example, by column chromatography using antibodies against the tag as an affinity matrix. Optionally, the tag can subsequently be removed from the purified Factor Bb antibody by various means such as using certain peptidases for cleavage.

Flanking sequences can be homologous (i.e., from the same species and/or strain as the host cell), heterologous (i.e., from a species other than the host cell species or strain), hybrid (i.e., a combination of flanking sequences from more than one source), synthetic or native. As such, the source of a flanking sequence can be any prokaryotic or eukaryotic organism, any vertebrate or invertebrate organism, or any plant, provided that the flanking sequence is functional in, and can be activated by, the host cell machinery.

Flanking sequences useful in the vectors of this disclosure can be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence can be known. Here, the flanking sequence can be synthesized using the methods described herein for nucleic acid synthesis or cloning.

Whether all or only a portion of the flanking sequence is known, it can be obtained using polymerase chain reaction (PCR) and/or by screening a genomic library with a suitable probe such as an oligonucleotide and/or flanking sequence fragment from the same or another species. Where the flanking sequence is not known, a fragment of DNA containing a flanking sequence can be isolated from a larger piece of DNA that may contain, for example, a coding sequence or even another gene or genes. Isolation can be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. If the vector of choice does not contain an origin of replication site, one can be chemically synthesized based on a known sequence, and ligated into the vector. For example, the origin of replication from the plasmid pBR322 (New England Biolabs®, Beverly, Mass.) is suitable for most gram-negative bacteria, and various viral origins (e.g., SV40, polyoma, adenovirus, vesicular stomatitis virus (VSV), or papillomaviruses such as HPV or BPV) are useful for cloning vectors in mammalian cells. Generally, the origin of replication component is not needed for mammalian expression vectors (for example, the SV40 origin is often used only because it also contains the virus early promoter).

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, glutamine synthetase (GS) and the tetracycline resistance gene. Advantageously, a neomycin resistance gene may also be used for selection in both prokaryotic and eukaryotic host cells.

Other selectable genes can be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include dihydrofolate reductase (DHFR) and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes another gene, such as an antibody that binds to a Factor Bb polypeptide or Factor Bb epitope. As a result, increased quantities of a polypeptide such as a Factor Bb antibody are synthesized from the amplified DNA.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

In some cases, such as where glycosylation is desired in a eukaryotic host cell expression system, one may manipulate the various pre- or prosequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide, if the enzyme cuts at such area within the mature polypeptide.

Expression and cloning vectors of the disclosure will typically contain a promoter that is recognized by the host organism and operably linked to the molecule encoding the Factor Bb antibody. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe gene to which they are operably linked, that is, with little or no control over gene expression. A large number of promoters, recognized by a variety of potential host cells, are well known. A suitable promoter is operably linked to the DNA encoding heavy chain or light chain comprising a Factor Bb antibody of the disclosure by removing the promoter from the source DNA by restriction enzyme digestion and inserting the desired promoter sequence into the vector.

In some embodiment, yeast cells may be used to produce the presently disclosed Factor Bb antibodies. Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which can be of interest include, but are not limited to: SV40 early promoter (Benoist and Chambon, 1981, *Nature* 290:304-310); CMV promoter (Thomsen et al., 1984, *Proc. Natl. Acad. U.S.A.* 81:659-663); the promoter contained in the 3' long terminal repeat of Rous sarcoma virus (Yamamoto et al., 1980, *Cell* 22:787-797); herpes thymidine kinase promoter (Wagner et al., 1981, *Proc. Natl. Acad. Sci. U.S.A.* 78:1444-1445); promoter and regulatory sequences from the metallothionine gene Prinster et al., 1982, *Nature* 296:39-42); and prokaryotic promoters such as the beta-lactamase promoter (Villa-Kamaroff et al., 1978, *Proc. Natl. Acad. Sci. U.S.A.* 75:3727-3731); or the tac promoter (DeBoer et al., 1983, *Proc. Natl. Acad. Sci. U.S.A.* 80:21-25). Also of interest are the following animal transcriptional control regions, which exhibit tissue specificity and have been utilized in transgenic animals: the elastase I gene control region that is active in pancreatic acinar cells (Swift et al., 1984, *Cell* 38:639-646; Ornitz et al., 1986, *Cold Spring Harbor Symp. Quant. Biol.* 50:399-409; MacDonald, 1987, *Hepatology* 7:425-515); the insulin gene control region that is active in pancreatic beta cells (Hanahan, 1985, *Nature* 315:115-122); the immunoglobulin gene control region that is active in lymphoid cells (Grosschedl et al., 1984, *Cell* 38:647-658; Adames et al., 1985, *Nature* 318:533-538; Alexander et al., 1987, *Mol. Cell. Biol.* 7:1436-1444); the mouse mammary tumor virus control region that is active in testicular, breast, lymphoid and mast cells (Leder et al., 1986, *Cell* 45:485-495); the albumin gene control region that is active in liver (Pinkert et al., 1987, *Genes and Devel.* 1:268-276); the alpha-feto-protein gene control region that is active in liver (Krumlauf et al., 1985, *Mol. Cell. Biol.* 5:1639-1648; Hammer et al., 1987, *Science* 253:53-58); the alpha 1-antitrypsin gene control region that is active in liver (Kelsey et al., 1987, *Genes and Devel.* 1:161-171); the beta-globin gene control region that is active in myeloid cells (Mogram et al., 1985, *Nature* 315:338-340; Kollias et al., 1986, *Cell* 46:89-94); the myelin basic protein gene control region that is active in oligodendrocyte cells in the brain (Readhead et al., 1987, *Cell* 48:703-712); the myosin light chain-2 gene control region that is active in skeletal muscle (Sani, 1985, *Nature* 314:283-286); and the gonadotropic releasing hormone gene control region that is active in the hypothalamus (Mason et al., 1986, *Science* 234:1372-1378).

An enhancer sequence can be inserted into the vector to increase transcription of DNA encoding light chain or heavy chain comprising a Factor Bb antibody of the disclosure by higher eukaryotes. Enhancers are cis-acting elements of DNA, usually about 10-300 bp in length, that act on the promoter to increase transcription. Enhancers are relatively orientation and position independent, having been found at positions both 5' and 3' to the transcription unit. Several enhancer sequences available from mammalian genes are known (e.g., globin, elastase, albumin, alpha-feto-protein and insulin). Typically, however, an enhancer from a virus is used. The SV40 enhancer, the cytomegalovirus early promoter enhancer, the polyoma enhancer, and adenovirus enhancers known in the art are exemplary enhancing elements for the activation of eukaryotic promoters. While an enhancer can be positioned in the vector either 5' or 3' to a coding sequence, it is typically located at a site 5' from the promoter. A sequence encoding an appropriate native or heterologous signal sequence (leader sequence or signal peptide) can be incorporated into an expression vector, to promote extracellular secretion of the antibody. The choice of signal peptide or leader depends on the type of host cells in which the antibody is to be produced, and a heterologous signal sequence can replace the native signal sequence. Examples of signal peptides that are functional in mammalian host cells include the following: the signal sequence for interleukin-7 (IL-7) described in U.S. Pat. No. 4,965,195; the signal sequence for interleukin-2 receptor described in Cosman et al., 1984, *Nature* 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

Expression vectors, for expressing the presently claimed antibodies of the disclosure can be constructed from a starting vector such as a commercially available vector. Such vectors may or may not contain all of the desired flanking sequences. Where one or more of the flanking sequences described herein are not already present in the vector, they can be individually obtained and ligated into the vector. Methods used for obtaining each of the flanking sequences are well known to one skilled in the art.

After the vector has been constructed and a nucleic acid molecule encoding light chain, a heavy chain, or a light chain and a heavy chain comprising an Factor Bb antigen binding sequence has been inserted into the proper site of the vector, the completed vector can be inserted into a suitable host cell for amplification and/or polypeptide expression. The transformation of an expression vector for a Factor Bb antibody into a selected host cell can be accomplished by well known methods including transfection, infection, calcium phosphate co-precipitation, electroporation, microinjection, lipofection, DEAE-dextran mediated transfection, or other known techniques. The method selected will in part be a function of the type of host cell to be used. These methods and other suitable methods are well known to the skilled artisan, and are set forth, for example, in Sambrook et al., 2001, supra.

A host cell, when cultured under appropriate conditions, synthesizes a Factor Bb antibody that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule. A host cell can be eukaryotic or prokaryotic.

Mammalian cell lines available as hosts for expression are well known in the art and include, but are not limited to, immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines can be selected through determining which cell lines have high expression levels and constitutively produce antibodies with Factor Bb binding properties. In another embodiment, a cell line from the B cell lineage that does not make its own antibody but has a capacity to make and secrete a heterologous antibody can be selected.

Use of Factor Bb Antibodies for Diagnostic and Therapeutic Purposes

Antibodies of the disclosure are useful for detecting Factor Bb in biological samples and identification of cells or tissues that produce Factor Bb protein. For example, the Factor Bb antibodies of the disclosure can be used in diagnostic assays, e.g., binding assays to detect and/or quantify Factor Bb expressed in a tissue or cell. Increased levels of Factor Bb may be an indication of diseases such as ocular disorders, cancer, infection, and/or ulcerative colitis. Decreased levels of Factor Bb may be in indication of cirrhosis, glomerulonephritis, hereditary angioedema, hepatitis, kidney transplant rejection, lupus nephritis, malnutrition, and/or systemic lupus erythematosis.

In some embodiments, the antibodies of the disclosure that specifically bind to Factor Bb can be used in treatment of Factor Bb mediated diseases in a patient in need thereof. In addition, the Factor Bb antibody of the disclosure can be used to inhibit Factor Bb from forming a complex with other complement proteins, thereby modulating the biological activity of Factor Bb in a cell or tissue. Antibodies that bind to Factor Bb thus can modulate and/or block interaction with other binding compounds and as such may have therapeutic use in ameliorating Factor Bb mediated diseases.

In some embodiments, Factor Bb antibodies may block the protease activity of Factor Bb. In some cases, the binding of Factor Bb by Factor Bb antibodies may result in disruption of the Factor Bb induced signal transduction cascade.

Diagnostic Methods

The antibodies of the disclosure can be used for diagnostic purposes to detect, diagnose, or monitor diseases and/or conditions associated with Factor Bb or Factor B. The disclosure provides for the detection of the presence of Factor Bb in a sample using classical immunohistological methods known to those of skill in the art (e.g., Tijssen, 1993, *Practice and Theory of Enzyme Immunoassays*, vol 15 (Eds R. H. Burdon and P. H. van Knippenberg, Elsevier, Amsterdam); Zola, 1987, *Monoclonal Antibodies: A Manual of Techniques*, pp. 147-158 (CRC Press, Inc.); Jalkanen et al., 1985, *J. Cell. Biol.* 101:976-985; Jalkanen et al., 1987, *J. Cell Biol.* 105:3087-3096). The detection of Factor Bb can be performed in vivo or in vitro.

Diagnostic applications provided herein include use of the antibodies to detect expression of Factor Bb and/or binding to Factor Bb. Examples of methods useful in the detection of the presence of Factor Bb include immunoassays, such as the enzyme linked immunosorbent assay (ELISA) and the radioimmunoassay (RIA).

For diagnostic applications, the antibody typically can be labeled with a detectable labeling group. Suitable labeling groups include, but are not limited to, the following: radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In some embodiments, the labelling group is coupled to the antibody via spacer arms of various lengths to reduce potential steric hindrance. Various methods for labelling proteins are known in the art and can be used in performing the present disclosure.

One aspect of the disclosure provides for identifying a cell or cells that express Factor Bb. In a specific embodiment, the antibody is labeled with a labeling group and the binding of the labeled antibody to Factor Bb is detected. In a further specific embodiment, the binding of the antibody to Factor Bb can be detected in vivo. In a further specific embodiment, the antibody/Factor Bb complex is isolated and measured using techniques known in the art. See, for example, *Harlow and Lane*, 1988, *Antibodies: A Laboratory Manual*, New York: Cold Spring Harbor (ed. 1991 and periodic supplements); John E. Coligan, ed., 1993, *Current Protocols In Immunology* New York: John Wiley & Sons.

Another aspect of the disclosure provides for detecting the presence of a test molecule that competes for binding to Factor Bb with the antibodies of the disclosure. An example of one such assay would involve detecting the amount of free antibody in a solution containing an amount of Factor Bb in the presence or absence of the test molecule. An increase in the amount of free antibody (i.e., the antibody not bound to Factor Bb) would indicate that the test molecule is capable of competing for Factor Bb binding with the antibody. In one embodiment, the antibody is labeled with a labeling group. Alternatively, the test molecule is labeled and the amount of free test molecule is monitored in the presence and absence of an antibody.

Indications

The complement system has been implicated in contributing to several acute and chronic conditions, including atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Bane syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation, and macular degeneration.

Macular degenerative diseases, such as all stages of age-related macular degeneration (AMD), including dry and wet (non-exudative and exudative) forms, choroidal neovascularization (CNV), uveitis, diabetic and other ischemia-related retinopathies, and other intraocular neovascular diseases, such as diabetic macular edema, pathological myopia, von Hippel-Lindau disease, histoplasmosis of the eye, Central Retinal Vein Occlusion (CRVO), Branched Retinal Vein Occlusion (BRVO), corneal neovascularization, and retinal neovascularization. A preferred group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

The presently disclosed anti-Factor Bb antibodies can be used in combination with one or more cytokines, lymphokines, hematopoietic factor(s), and/or an anti-inflammatory agent.

Treatment of the diseases and disorders recited herein can include the use of first line drugs for control of pain and inflammation in combination (pretreatment, post-treatment, or concurrent treatment) with treatment with one or more of the antibodies provided herein. These drugs are classified as non-steroidal, anti-inflammatory drugs (NSAIDs). Secondary treatments include corticosteroids, slow acting antirheumatic drugs (SAARDs), or disease modifying (DM) drugs. Information regarding the following compounds can be found in The Merck Manual of Diagnosis and Therapy, Sixteenth Edition, Merck, Sharp & Dohme Research Laboratories, Merck & Co., Rahway, N.J. (1992) and in Pharmaprojects, PJB Publications Ltd.

In a specific embodiment, the present disclosure is directed to the use of an antibody and any of one or more NSAIDs for the treatment of the diseases and disorders recited herein. NSAIDs owe their anti-inflammatory action, at least in part, to the inhibition of prostaglandin synthesis (Goodman and Gilman in "The Pharmacological Basis of Therapeutics," MacMillan 7th Edition (1985)). NSAIDs can be characterized into at least nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones.

In another specific embodiment, the present disclosure is directed to the use of an antibody in combination (pretreatment, post-treatment, or concurrent treatment) with any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate, magnesium salicylate, choline salicylate, diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide 0-acetic acid, salsalate, sodium salicylate and sulfasalazine. Structurally related salicylic acid derivatives having similar analgesic and anti-inflammatory properties are also intended to be encompassed by this group.

In an additional specific embodiment, the present disclosure is directed to the use of an antibody in combination (pretreatment, post-treatment, or concurrent treatment) with any of one or more propionic acid derivatives, prodrug esters or pharmaceutically acceptable salts thereof. The propionic acid derivatives, prodrug esters, and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, naproxen sodium, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group.

In yet another specific embodiment, the present disclosure is directed to the use of an antibody in combination (pretreatment, post-treatment, or concurrent treatment) with any of one or more acetic acid derivatives, prodrug esters or pharmaceutically acceptable salts thereof. The acetic acid derivatives, prodrug esters, and pharmaceutically acceptable salts thereof comprise: acemetacin, alclofenac, amfenac, bufexamac, cinmetacin, clopirac, delmetacin, diclofenac potassium, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, tolmetin sodium, zidometacin and zomepirac. Structurally related acetic acid derivatives having similar analgesic and anti-inflammatory properties are also intended to be encompassed by this group.

In another specific embodiment, the present disclosure is directed to the use of an antibody in combination (pretreatment, post-treatment, or concurrent treatment) with any of one or more fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenamate sodium, medofenamic acid, mefenamic acid, niflumic acid, talniflumate, terofenamate, tolfenamic acid and ufenamate. Structurally related fenamic acid derivatives having similar analgesic and anti-inflammatory properties are also intended to be encompassed by this group.

In an additional specific embodiment, the present disclosure is directed to the use of an antibody in combination (pretreatment, post-treatment, or concurrent treatment) with any of one or more carboxylic acid derivatives, prodrug esters or pharmaceutically acceptable salts thereof. The carboxylic acid derivatives, prodrug esters, and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group.

In yet another specific embodiment, the present disclosure is directed to the use of an antibody in combination (pretreatment, post-treatment, or concurrent treatment) with any of one or more butyric acid derivatives, prodrug esters or pharmaceutically acceptable salts thereof. The butyric acid derivatives, prodrug esters, and pharmaceutically acceptable salts thereof comprise: bumadizon, butibufen, fenbufen and xenbucin. Structurally related butyric acid derivatives having similar analgesic and anti-inflammatory properties are also intended to be encompassed by this group.

In another specific embodiment, the present disclosure is directed to the use of an antibody in combination (pretreatment, post-treatment, or concurrent treatment) with any of one or more oxicams, prodrug esters, or pharmaceutically acceptable salts thereof. The oxicams, prodrug esters, and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

In still another specific embodiment, the present disclosure is directed to the use of an antibody in combination (pretreatment, post-treatment, or concurrent treatment) with any of one or more pyrazoles, prodrug esters, or pharmaceutically acceptable salts thereof. The pyrazoles, prodrug esters, and pharmaceutically acceptable salts thereof which can be used comprise: difenamizole and epirizole. Structurally related pyrazoles having similar analgesic and anti-inflammatory properties are also intended to be encompassed by this group.

In an additional specific embodiment, the present disclosure is directed to the use of an antibody in combination (pretreatment, post-treatment or, concurrent treatment) with any of one or more pyrazolones, prodrug esters, or pharmaceutically acceptable salts thereof. The pyrazolones, prodrug esters and pharmaceutically acceptable salts thereof which can be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

In another specific embodiment, the present disclosure is directed to the use of an antibody in combination (pretreatment, post-treatment, or concurrent treatment) with any of one or more of the following NSAIDs: ε-acetamidocaproic acid, S-adenosyl-methionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isoniximn, lefetamine HCl, leflunomide, lofemizole, lotifazole, lysin clonixinate, meseclazone, nabumetone, nictindole, nimesulide, orgotein, orpanoxin, oxaceprol, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the NSAIDs are also intended to be encompassed by this group.

In still another specific embodiment, the present disclosure is directed to the use of an antibody in combination (pretreatment, post-treatment or concurrent treatment) with any of one or more corticosteroids, prodrug esters or pharmaceutically acceptable salts thereof for the treatment of the diseases and disorders recited herein, including acute and chronic inflammation such as rheumatic diseases, graft versus host disease and multiple sclerosis. Corticosteroids, prodrug esters and pharmaceutically acceptable salts thereof include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flucinolone acetonide, flunisolide, fluocinonide, fluorocinolone acetonide, fluocortin butyl, fluocortolone, fluocortolone hexanoate, diflucortolone valerate, fluorometholone, fluperolone acetate, fluprednidene acetate, fluprednisolone, flurandenolide, formocortal, halcinonide, halometasone, halopredone acetate, hydro-cortamate, hydrocortisone, hydrocortisone acetate, hydro-cortisone butyrate, hydrocortisone phosphate, hydrocortisone 21-sodium succinate, hydrocortisone tebutate, mazipredone, medrysone, meprednisone, methylprednisolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

In another specific embodiment, the present disclosure is directed to the use of an antibody in combination (pretreatment, post-treatment, or concurrent treatment) with any of one or more slow-acting antirheumatic drugs (SAARDs) or disease modifying antirheumatic drugs (DMARDS), prodrug esters, or pharmaceutically acceptable salts thereof for the treatment of the diseases and disorders recited herein, including acute and chronic inflammation such as rheumatic diseases, graft versus host disease and multiple sclerosis. SAARDs or DMARDS, prodrug esters and pharmaceutically acceptable salts thereof comprise: allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclo-phosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxychloroquine sulfate, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

In another specific embodiment, the present disclosure is directed to the use of an antibody in combination (pretreatment, post-treatment, or concurrent treatment) with any of one or more COX2 inhibitors, prodrug esters or pharmaceutically acceptable salts thereof for the treatment of the diseases and disorders recited herein, including acute and chronic inflammation. Examples of COX2 inhibitors, prodrug esters or pharmaceutically acceptable salts thereof include, for example, celecoxib. Structurally related COX2 inhibitors having similar analgesic and anti-inflammatory properties are also intended to be encompassed by this group. Examples of COX-2 selective inhibitors include but not limited to etoricoxib, valdecoxib, celecoxib, licofelone, lumiracoxib, rofecoxib, and the like.

In still another specific embodiment, the present disclosure is directed to the use of an antibody in combination (pretreatment, post-treatment, or concurrent treatment) with any of one or more antimicrobials, prodrug esters or pharmaceutically acceptable salts thereof for the treatment of the diseases and disorders recited herein, including acute and chronic inflammation. Antimicrobials include, for example, the broad classes of penicillins, cephalosporins and other beta-lactams, aminoglycosides, azoles, quinolones, macrolides, rifamycins, tetracyclines, sulfonamides, lincosamides and polymyxins. The penicillins include, but are not limited to penicillin G, penicillin V, methicillin, nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams include, but are not limited to cephalothin, cephapirin, cephalexin, cephradine, cefazolin, cefadroxil, cefaclor, cefamandole, cefotetan, cefoxitin, ceruroxime, cefonicid, ceforadine, cefixime, cefotaxime, moxalactam, ceftizoxime, cetriaxone, cephoperazone, ceftazidime, imipenem and aztreonam. The aminoglycosides include, but are not limited to streptomycin, gentamicin, tobramycin, amikacin, netilmicin, kanamycin and neomycin. The azoles include, but are not limited to fluconazole. The quinolones include, but are not limited to nalidixic acid, norfloxacin, enoxacin, ciprofloxacin, ofloxacin, sparfloxacin and temafloxacin. The macrolides include, but are not limited to erythomycin, spiramycin and azithromycin. The rifamycins include, but are not limited to rifampin. The tetracyclines include, but are not limited to spicycline, chlortetracycline, clomocycline, demeclocycline, deoxycycline, guamecycline, lymecycline, meclocycline, methacycline, minocycline, oxytetracycline, penimepicycline, pipacycline, rolitetracycline, sancycline, senociclin and tetracycline. The sulfonamides include, but are not limited to sulfanilamide, sulfamethoxazole, sulfacetamide, sulfadiazine, sulfisoxazole and co-trimoxazole (trimethoprim/sulfamethoxazole). The lincosamides include, but are not limited to clindamycin and lincomycin. The polymyxins (polypeptides) include, but are not limited to polymyxin B and colistin.

Methods of Treatment: Pharmaceutical Formulations, Routes of Administration

Compositions are disclosed comprising a therapeutically effective amount of one or a plurality of the antibodies of the disclosure together with a pharmaceutically acceptable diluent, carrier, solubilizer, emulsifier, preservative, and/or adjuvant. In addition, the disclosure provides methods of treating a patient by administering such pharmaceutical composition. A patient can be either a human subject or an animal subject.

Pharmaceutical compositions comprising one or more antibodies can be used to reduce Factor Bb activity. Pharmaceutical compositions comprising one or more antibodies can be used in treating the consequences, symptoms, and/or the pathology associated with Factor Bb activity. Pharmaceutical compositions comprising one or more antibodies can be used in methods of inhibiting the complement pathway and/or Factor Bb binding to other complement proteins. In certain embodiments, the antibody inhibits protease activity of Factor Bb. In additional embodiments, pharmaceutical compositions comprising one or more antibodies can be used in methods of inhibiting Factor Bb protease activity. Pharmaceutical compositions comprising one or more antibodies can be used in methods of treating the consequences, symptoms, and/or the pathology associated with Factor Bb activity. Pharmaceutical compositions comprising one or more antibodies can be used in methods of inhibiting the production MAC. Pharmaceutical compositions comprising one or more antibodies can be used in methods of inhibiting Macular Degeneration.

Preferably, acceptable formulation materials are nontoxic to recipients at the dosages and concentrations employed. In specific embodiments, pharmaceutical compositions comprising a therapeutically effective amount of Factor Bb antibodies are provided.

In certain embodiments, acceptable formulation materials preferably are nontoxic to recipients at the dosages and concentrations employed. In certain embodiments, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See, REMINGTON'S PHARMACEUTICAL SCIENCES, 18th Edition, (A. R. Genrmo, ed.), 1990, Mack Publishing Company.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibodies of the disclosure. In certain embodiments, the primary vehicle or carrier in a pharmaceutical composition can be either aqueous or non-aqueous in nature. For example, a suitable vehicle or carrier can be water for injection, physiological saline solution or artificial cerebrospinal fluid, possibly supplemented with other materials common in compositions for parenteral administration. Neutral buffered saline or saline mixed with serum albumin are further exemplary vehicles. In specific embodiments, pharmaceutical compositions comprise Tris buffer of about pH 7.0-8.5, or acetate buffer of about pH 4.0-5.5, and may further include sorbitol or a suitable substitute therefor. In certain embodiments of the disclosure, Factor Bb antibody compositions can be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the Factor Bb antibody product can be formulated as a lyophilizate using appropriate excipients such as sucrose.

The pharmaceutical compositions of the disclosure can be selected for parenteral delivery. Alternatively, the compositions can be selected for inhalation or for delivery through the digestive tract, such as orally. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this disclosure can be provided in the form of a pyrogen-free, parenterally acceptable aqueous solution comprising the desired Factor Bb antibody in a pharmaceutically acceptable vehicle. A particularly suitable vehicle for parenteral injection is sterile distilled water in which the Factor Bb antibody is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices can be used to introduce the desired antibody.

Pharmaceutical compositions of the disclosure can be formulated for inhalation. In these embodiments, Factor Bb antibodies are advantageously formulated as a dry, inhalable powder. In specific embodiments, Factor Bb antibody inhalation solutions may also be formulated with a propellant for aerosol delivery. In certain embodiments, solutions can be nebulized. Pulmonary administration and formulation methods therefore are further described in International Patent Application No. PCT/US94/001875, which is incorporated by reference and describes pulmonary delivery of chemically modified proteins. It is also contemplated that formulations can be administered orally. Factor Bb antibodies that are administered in this fashion can be formulated with or without carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. Additional agents can be included to facilitate absorption of the Factor Bb antibody. Diluents, flavorings, low melting point waxes, vegetable oils, lubricants, suspending agents, tablet disintegrating agents, and binders may also be employed.

A pharmaceutical composition of the disclosure is preferably provided to comprise an effective quantity of one or a plurality of Factor Bb antibodies in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving Factor Bb antibodies in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 2:547-556), poly (2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, *Proc. Natl. Acad. Sci. U.S.A.* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method can be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, crystal, or as a dehydrated or lyophilized powder. Such formulations can be stored either in a ready-to-use form or in a form (e.g., lyophilized) that is reconstituted prior to administration. The disclosure also provides kits for producing a single-dose administration unit. The kits of the disclosure may each contain both a first container having a dried protein and a second container having an aqueous formulation. In certain embodiments of this disclosure, kits containing single and multi-chambered pre-filled syringes (e.g., liquid syringes and lyosyringes) are provided.

The therapeutically effective amount of a Factor Bb antibody-containing pharmaceutical composition to be employed will depend, for example, upon the therapeutic context and objectives. One skilled in the art will appreciate that the appropriate dosage levels for treatment will vary depending, in part, upon the molecule delivered, the indication for which the Factor Bb antibody is being used, the route of administration, and the size (body weight, body surface or organ size) and/or condition (the age and general health) of the patient. In certain embodiments, the clinician may titer the dosage and modify the route of administration to obtain the optimal therapeutic effect. A typical dosage may range from about 0.1 μg/kg to up to about 30 mg/kg or more, depending on the factors mentioned above. In specific embodiments, the dosage may range from 0.1 μg/kg up to about 30 mg/kg, optionally from 1 μg/kg up to about 30 mg/kg or from 10 μg/kg up to about 5 mg/kg.

Dosing frequency will depend upon the pharmacokinetic parameters of the particular Factor Bb antibody in the formulation used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data. In certain embodiments, the antibodies of the disclosure can be administered to patients throughout an extended time period. Chronic administration of an antibody of the disclosure minimizes the adverse immune or allergic response commonly associated with antibodies that are not fully human, for example an antibody raised against a human antigen in a non-human animal, for example, a non-fully human antibody or non-human antibody produced in a non-human species.

The route of administration of the pharmaceutical composition is in accord with known methods, e.g., orally, through injection by intravenous, intraperitoneal, intracerebral (intra-parenchymal), intracerebroventricular, intramuscular, intra-ocular, intravitreal, sub-retinal, intraarterial, intraportal, or intralesional routes; by sustained release systems or by implantation devices. In certain embodiments, the compositions can be administered by bolus injection or continuously by infusion, or by implantation device.

The composition also can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. For ocular implants, the implant can be implanted via intra-ocular injection, intravitreal injection, sub-retinal injection, suprachoroidal injection, retrobulbar injection or injection into sub-Tenon space.

It also can be desirable to use Factor Bb antibody pharmaceutical compositions according to the disclosure ex vivo. In such instances, cells, tissues or organs that have been removed from the patient are exposed to Factor Bb antibody pharmaceutical compositions after which the cells, tissues and/or organs are subsequently implanted back into the patient.

In particular, Factor Bb antibodies can be delivered by implanting certain cells that have been genetically engineered, using methods such as those described herein, to express and secrete the Factor Bb antibody. In certain embodiments, such cells can be animal or human cells, and can be autologous, heterologous, or xenogeneic. In certain embodiments, the cells can be immortalized. In other embodiments, in order to decrease the chance of an immunological response, the cells can be encapsulated to avoid infiltration of surrounding tissues. In further embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

All references cited within the body of the instant specification are hereby expressly incorporated by reference in their entirety.

EXAMPLES

The following examples, including the experiments conducted and the results achieved, are provided for illustrative purposes only and are not to be construed as limiting the disclosure.

Example 1—Binding Assay of Anti-Factor Bb Antibody Compared to Anti-Factor B Antibody Bio-Layer Interferometry (BLI), a label-free technology was used for measuring the binding kinetics of Factor Bb (CompTech®) and human Factor B antigen (CompTech®) with anti-Factor Bb monoclonal antibody. Affinity measurements were performed with Octet® QK$^e$ equipped with Anti-human IgG Fc capture (AHC) biosensor tips (FortéBio, Menlo Park, Calif., USA). The assay was performed at 30° C. in 1×PBS buffer (Gibco®, PBS pH 7.2). Samples were agitated at 1000 rpm. Prior to analysis, sensors were humidified for 15 minutes.

Purified anti-Factor Bb antibody was tested for its binding capacity with AHC sensor tips. Tips were loaded using 20 μg/ml of anti-Factor Bb antibody. Loading proceeded for 300 s resulting in capture levels of between 1.8 and 2 nm. Factor Bb or Factor B antigens were prepared for binding analysis by dilution to concentrations of 50 nM in 1×PBS. Association was initiated and monitored for 200 s, after which tips were transferred to 1×PBS buffer without Factor protein (Gibco®, PBS pH 7.2), in order to monitor dissociation. Sensor data was collected throughout the experiments, processed, and analyzed using the Octet data analysis software 7 (FortéBio).

Selectivity of anti-factor Bb antibody was first tested by comparing binding on-rates for Factor Bb and Factor B proteins. This analysis was performed using the Octet® QK$^e$ system from FortèBio. The binding, measured over 200 s in protein preparations of 50 nM, indicate that the anti-factor Bb antibody specifically binds to Factor Bb, but binding to Factor B is significantly lower (FIG. 1).

Example 2—Functional Assay of Anti-Factor Bb Monoclonal Antibody

Hemolysis Assay—

Activation of the alternative pathway of (AP) requires higher concentrations of serum than the classical pathway. Generally, a final concentration of 5 mM Mg++ in the presence of 5 mM EGTA is used in the assays where the EGTA chelates Ca++ preferentially. The AP of most mammalian species is activated spontaneously by rabbit erythrocytes so they are a convenient target. Prepare rabbit erythrocytes (Complement Technology, Inc.) by washing 3 times with GVB0 (CompTech® product) and resuspending into 5×108/ml. Different amount of anti-factor Bb antibody was diluted with GVB0. Mix the 100 ul reaction on ice in the order of serial diluted anti-factor Bb antibody, 0.1M MgEGTA (CompTech® product), 1/2NHS (normal human serum diluted 1/2 with GVB0), and rabbit Er. Then, incubate the reaction at 37° C. for 30 minutes on a shaker. Add 1.0 ml cold GVBE. Mix and centrifuge for 3 min at approx. 1000×g, or higher, to pellet cells. Transfer 100 ul of the supernatant to a 96-well plate and read at 412 nm (SoftMax® Pro 4.7.1). Data was analyzed using GraphPad Prism 4.

Results—

Figure 2:
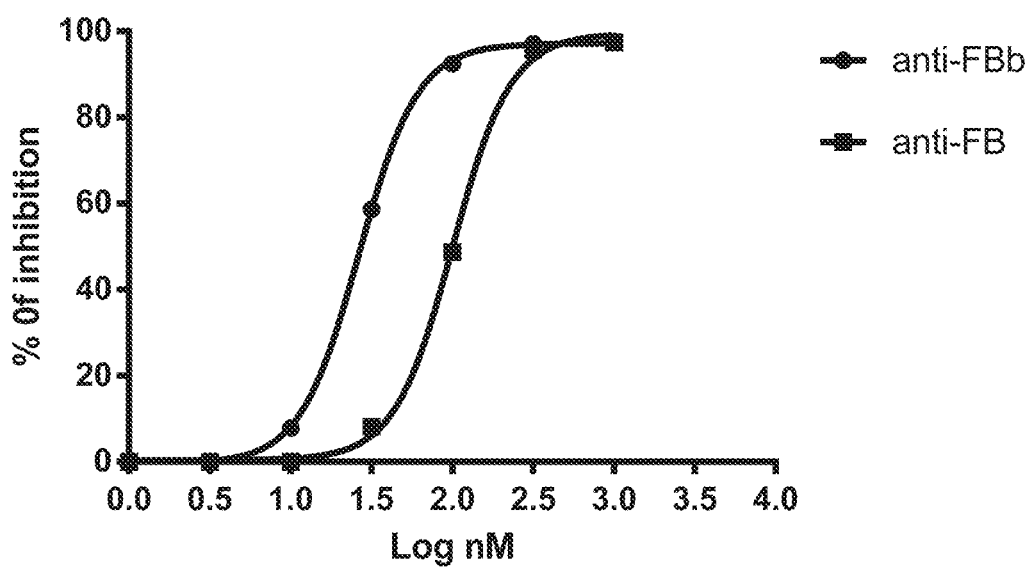
FIG. 2 shows the results of a hemolysis assay using either anti-Factor B or anti-Factor Bb antibodies in the presence of 10% normal human serum.
Figure 3:
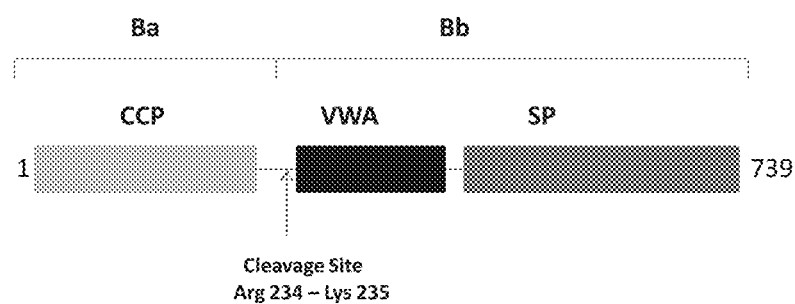
FIG. 3 shows a diagram of the Complement Factor B structure.

To determine the potency of anti-factor Bb antibodies, AP hemolysis assay was performed and the IC50 nM (the amount of the antibody necessary to inhibit 50% of the hemolysis reaction). The data indicated that the IC50 of the presently disclosed anti-Factor Bb antibody is about 40 nM, whereas IC50 of anti-Factor B antibody is about 100 nM (FIG. 2). Thus, anti-Factor Bb antibody is about ten times more potent than anti-Factor B antibody in AP hemolysis assay.

Example 3—In Vivo Efficacy Model

Humanized H4L4 99A12 antibody, (SEQ ID NOS:15 and 11 respectively), was tested in a non-human primate light injury model. Intravitreal dosing of the H4L4 99A12 antibody provided efficacy in blocking complement deposition in the retina relative to control. This data indicates that local delivery of the H4L4 99A12 antibody is efficacious in an in vivo model relevant to treatment in humans of macular degeneration and other ocular indications.

We claim:

1. A nucleic acid encoding an isolated antibody, wherein the antibody is a Factor Bb antibody, wherein the antibody comprises a heavy chain and a light chain, wherein the antibody binds to Factor Bb with greater affinity than to Factor B; and inhibits complement dependent hemolysis; and wherein either:

the light chain comprises an amino acid sequence selected from the group consisting of SEQ ID NO:8-11; and wherein the heavy chain comprises an amino acid sequence selected from the group consisting of SEQ ID NO: 12-15;

or the light chain comprises an amino acid sequence to a sequence selected from the group consisting of SEQ ID NO:24-27; and wherein the heavy chain comprises an amino acid sequence selected from the group consisting of SEQ ID NO:28-31.

2. The nucleic acid of claim 1, wherein the antibody binds Factor Bb with a $K_d$ of less than about 1 nM.

3. The nucleic acid of claim 1, wherein the antibody blocks formation of membrane attack complex (MAC) in a patient.

4. The nucleic acid of claim 1, wherein the antibody comprises a light chain variable domain and a heavy chain variable domain selected from the light and heavy chain variable domain amino acid sequences: SEQ ID NO:8/SEQ ID NO:12; SEQ ID NO:8/SEQ ID NO:13; SEQ ID NO:8/ SEQ ID NO:14; SEQ ID NO:8/SEQ ID NO:15; SEQ ID NO:9/SEQ ID NO:12; SEQ ID NO:9/SEQ ID NO:13; SEQ ID NO:9/SEQ ID NO:14; SEQ ID NO:9/SEQ ID NO:15; SEQ ID NO:10/SEQ ID NO:12; SEQ ID NO:10/SEQ ID NO:13; SEQ ID NO:10/SEQ ID NO:14; and SEQ ID NO:10/SEQ ID NO:15; SEQ ID NO:11/SEQ ID NO:12; SEQ ID NO:11/SEQ ID NO:13; SEQ ID NO:11/SEQ ID NO:14; and SEQ ID NO:11/SEQ ID NO:15.

5. The nucleic acid of claim 1, wherein the antibody comprises a light chain variable domain and a heavy chain variable domain selected from the light chain and heavy chain variable domain amino acid sequences: SEQ ID NO:24/SEQ ID NO:28; SEQ ID NO:24/SEQ ID NO:29; SEQ ID NO:24/SEQ ID NO:30; SEQ ID NO:24/SEQ ID NO:31; SEQ ID NO:25/SEQ ID NO:28; SEQ ID NO:25/ SEQ ID NO:29; SEQ ID NO:25/SEQ ID NO:30; SEQ ID NO:25/SEQ ID NO:31; SEQ ID NO:26/SEQ ID NO:28; SEQ ID NO:26/SEQ ID NO:29; SEQ ID NO:26/SEQ ID NO:30; and SEQ ID NO:26/SEQ ID NO:31; SEQ ID NO:27/SEQ ID NO:28; SEQ ID NO:27/SEQ ID NO:29; SEQ ID NO:27/SEQ ID NO:30; and SEQ ID NO:27/SEQ ID NO:31.

6. The nucleic acid of claim 1 wherein the antibody comprises a light chain variable domain amino acid sequence of SEQ ID NO:11 and a heavy chain variable domain amino acid sequence of SEQ ID NO:15.

7. The nucleic acid of claim 1, wherein said antibody is a monoclonal antibody, a polyclonal antibody, a recombinant antibody, a humanized antibody, a chimeric antibody, a multispecific antibody, or an antibody fragment thereof.

8. The nucleic acid of claim 7, wherein said antibody fragment is a Fab fragment, a Fab' fragment, a F(ab')2 fragment, a Fv fragment, a diabody, or a single chain antibody molecule.

9. The nucleic acid of claim 7, wherein said antibody is of the IgG1-, IgG2- IgG3- or IgG4-type.

* * * * *